(12) United States Patent
Kotsuka et al.

(10) Patent No.: US 6,881,761 B2
(45) Date of Patent: Apr. 19, 2005

(54) POROUS POLYMER PARTICLE, ANION EXCHANGER, PRODUCING METHOD THEREOF, COLUMN FOR ION CHROMATOGRAPHY, AND METHOD FOR MEASURING ANIONS

(75) Inventors: Takashi Kotsuka, Kanagawa (JP); Kuniaki Shimbo, Kanagawa (JP); Hiroshi Suzuki, Kanagawa (JP); Hisako Sakuma, Düsseldorf (DE); Toshio Tokuda, Tokyo (JP)

(73) Assignee: Showa Denko K.K., Tokyo (JP)

( * ) Notice: Subject to any disclaimer, the term of this patent is extended or adjusted under 35 U.S.C. 154(b) by 500 days.

(21) Appl. No.: 09/799,806

(22) Filed: Mar. 7, 2001

(65) Prior Publication Data
US 2002/0004535 A1 Jan. 10, 2002

Related U.S. Application Data

(60) Provisional application No. 60/262,065, filed on Jan. 18, 2001, provisional application No. 60/262,043, filed on Jan. 18, 2001, and provisional application No. 60/213,257, filed on Jun. 22, 2000.

(30) Foreign Application Priority Data

May 29, 2000 (JP) ........................ 2000-158367
Dec. 19, 2000 (JP) ........................ 2000-386002
Dec. 27, 2000 (JP) ........................ 2000-398094

(51) Int. Cl.⁷ ............................. C08F 8/30; B01D 15/08
(52) U.S. Cl. ............................. 521/32; 521/25; 521/29; 521/53; 525/60; 525/113; 525/375; 525/379; 525/380; 210/656; 210/660; 210/661; 210/683; 428/402
(58) Field of Search .................. 521/32, 25, 29, 521/53; 525/113, 375, 379, 380, 60; 210/683, 656, 660, 661; 428/402

(56) References Cited

U.S. PATENT DOCUMENTS

| 4,298,700 A | | 11/1981 | Takase | |
| 4,501,826 A | * | 2/1985 | Meitzner et al. | .............. 521/29 |
| 4,684,667 A | | 8/1987 | Hunter | |
| 5,158,603 A | * | 10/1992 | Stierman et al. | .......... 521/31 X |
| 5,936,003 A | * | 8/1999 | Pohl et al. | .................... 521/32 |

FOREIGN PATENT DOCUMENTS

| EP | 0 043 074 A | 1/1982 | |
| EP | 0 066 165 A | 12/1982 | |
| EP | 0 556 688 A | 8/1993 | |
| FR | 2 333 005 A | 6/1977 | |
| FR | 2 460 971 A | 1/1981 | |
| GB | 2 034 328 A | 6/1980 | |
| JP | 62-79356 | 4/1987 | .......... G01N/30/48 |
| JP | 63-61619 | 11/1988 | .......... G01N/30/48 |
| JP | 7-37972 | 4/1995 | .......... G01N/30/88 |
| JP | 9-124729 | 5/1997 | ............. C08F/8/00 |
| JP | 2000-180429 | 6/2000 | .......... G01N/30/26 |

OTHER PUBLICATIONS

English Language Translation of JP 52–35779 to Fujiwara et al, published 19770318.*
Chemical Abstracts, JP 77 035779, date Jul. 25, 1977.
Derwent Abstract, JP 09–077790, date Mar. 25, 1997.
Derwent Abstract, JP 2001–040032, date Feb. 13, 2001.

* cited by examiner

Primary Examiner—Fred Teskin
(74) Attorney, Agent, or Firm—Sughrue Mion, PLLC

(57) ABSTRACT

Disclosed are (1) a porous polymer particle comprising a polymer substrate having ester bonds connected to a group containing a quaternary ammonium structure through a spacer molecule, (2) an alkali-resistant, high-strength porous polymer particle having ester bonds connected to a group containing a quaternary ammonium structure through a spacer molecule, a part of the ester bonds being saponified and converted to a hydroxyl group(s), (3) a porous polymer particle comprising a polymer substrate having ester bonds connected to a group containing a quaternary ammonium structure through a spacer molecule, the porous polymer particles being treated with an alkaline solution to generate a hydroxyl and/or a carboxyl group on a surface of the substrate, (4) an anion exchanger comprising any one of the particles (1) to (3) above, (5) a packing material for anion chromatography comprising the anion exchanger (4) above, (6) a column for anion chromatography using the anion exchanger (4) above, and (7) a method for measuring anions using the anion exchanger (4) above.

35 Claims, 10 Drawing Sheets

POROUS POLYMER PARTICLE, ANION EXCHANGER, PRODUCING METHOD THEREOF, COLUMN FOR ION CHROMATOGRAPHY, AND METHOD FOR MEASURING ANIONS

CROSS-REFERENCE TO RELATED APPLICATIONS

This application is based on the provisions of 35 U.S.C. §111(a) with claiming the benefit of filing date of U.S. provisional application Ser. No. 60/213,257 filed on Jun. 22, 2000, U.S. provisional application Ser. No. 60/262,043 filed Jan. 18, 2001, and U.S. provisional application Ser. No. 60/262,065 filed Jan. 18, 2001 under the provisions of 35 U.S.C. §111(b), pursuant to 35 U.S.C. §119(e) (i), the disclosures of which are incorporated herein by reference.

TECHNICAL FIELD

The present invention relates to a porous polymer particle for anion analysis liquid chromatography, to anion exchanger comprising the particle, to a producing method thereof, to packing material for anion chromatography, to a column for anion chromatography, and to a method for measuring anions.

More particularly, the present invention relates to (1) a porous polymer particle having high mechanical strength useful for anion analysis liquid chromatography for a suppressor method and a non-suppressor method, and anion exchanger comprising the particles, and a producing method thereof, (2) a porous polymer particle that has alkali resistance and high-strength, can be adjusted for the position of occurrence of carbonate dip, and can be used in particularly for a suppressor method ion chromatography, anion exchanger comprising the particles, and a producing method thereof, (3) a porous polymer particle that enables with ease adjustment of retention time of anions to be measured in anion analysis ion chromatography for suppressor and non-suppressor methods, an anion exchanger comprising the particles, and a producing method thereof, (4) a packing material for anion chromatography using the anion exchanger of any one of (1) to (3) above, (5) a column for anion chromatography using the anion exchanger of any one of (1) to (3) above, and (6) a method for measuring anions using the anion exchanger of any one of (1) to (3) above.

BACKGROUND ART

In examination of water pollution, analysis of food and the like, analysis of 7 kinds of ions, i.e., fluoride ion ($F^-$), chloride ion ($Cl^-$), nitrite ion ($NO_2^-$), bromide ion ($Br^-$), nitrate ion ($NO_3^-$), sulfate ion ($SO_4^{2-}$), and phosphate ion ($PO_4^{3-}$) are important and called "7 standard inorganic anions". Recently, in the analysis of inorganic anions including the 7 standard inorganic anions, ion chromatography is being used as an efficient and high-precision/high-sensitive means for analyzing them.

In the ion chromatography, a sample containing an ion seed is injected into an ion exchange column while feeding an eluent into the column and the ions (kind, amount) separated and eluted from the column with a time gap due to the difference in the retention time are detected by a high-sensitivity detector such as electrical conductivity detector. The ion chromatography includes "a suppressor method" using a suppressor and "a non-suppressor method" using no suppressor.

In the non-suppressor method, organic acids having low conductivity such as phthalic acid, p-hydroxybenzoic acid, and trimesic acid are used and the anions are detected directly by a conductivity detector immediately after they were separated by a separation column. The conductivity detector is low in background so that high-sensitivity analysis is possible. The pH of the eluent is not particularly limited and various separation conditions can be selected.

Generally used packing (hereinafter, also referred to as "anion exchanger") of a column for a non-suppressor method includes chemical bond type ion exchangers comprising copolymer particles of a vinyl ester- or vinyl ether-containing monomer having a hydroxyl group and a vinyl ester- or vinyl ether-crosslinking monomer.

The column for a non-suppressor method that has been being conventionally used is packed with the above packing. In order to make the column high-powered, packing must be downsized than ever.

However, the above packing has insufficient mechanical strength and it has not been easy to reduce its particle diameter.

Under the circumstances, a first object of the present invention is to provide a porous polymer particles having high mechanical strength useful for anion analysis liquid chromatography for a suppressor method and a non-suppressor method, and anion exchanger comprising the particles and a producing method thereof.

On the other hand, in the ion chromatography by a suppressor method, a suppressor, which is an apparatus for substituting the cations in the liquid by hydrogen ions is used. As shown in FIG. 1, the suppressor is connected to between a separation column and a detector and functions to decrease the background and increase the sensitivity of measurement when detecting ions using an electrical conductivity detector.

In "the suppressor method", a mixed solution of sodium carbonate and sodium hydrogencarbonate, a borate buffer, an aqueous sodium hydroxide solution, an aqueous potassium hydroxide solution or the like is passed through as the eluent to separate the sample ion in the separation column and thereafter the ion separated is detected by an electrical conductivity detector through a suppressor. The electrical conductivity measured by the detector includes the electrical conductivity of the eluent itself as the background and is comprehended as an superposed signal that comprises contributions of ion species in the sample. The suppressor converts a salt or base in the eluent to an acid or the like having a lower degree of dissociation to thereby decrease the background electrical conductivity and as a result improves the measurement sensitivity of signals attributable to the ion species of the sample.

Because of its high sensitivity, the suppressor method is indispensable to the management of pure water, chemicals and the like for use in the semiconductor art, though a dedicated apparatus is necessary and the profitability is inferior as compared with the non-suppressor method.

The anion exchanger used in the suppressor method is required to be stable at a relatively high pH (a pH on the order of from 9 to 12) and have a capability of successfully separating the objective anion. Specifically, the anion exchanger includes so-called pellicular-type ion exchanger obtained by coating an anion exchangeable latex on a sulfonated polystyrene substrate, and a porous chemical bond-type ion exchanger obtained by chemical-bonding a quaternary ammonium group to a porous polymer substrate, particularly an acrylate polymer substrate. Among these, the former ion exchanger has excellent alkali resistance and is being used on the greatest occasions. In the case of the latter ion exchanger, commercially available products at present are not sufficiently high in the alkali resistance and these are now scarcely used in the suppressor method but are used in many cases in the non-suppressor method mainly using an acidic eluent.

The pellicular-type ion exchanger restricts the migration of ions only to the surface of the packing and does not allow their entering into pores. Therefore, this ion exchanger is advantageous in that (1) the diffusion is almost prevented from occurring and (2) the ion does not interfere with the substrate. However, this ion exchanger is disadvantageous in that the usable surface area of the packing is limited in view of the structure and the column efficiency disadvantageously has a bound. For elevating the column efficiency of the pellicular-type ion exchanger, it is necessary to increase the column length or to reduce the particle size of the packing. However, the column used at present already has a large length of 250 mm and a more increase in the column length is not practical. With respect to the reduction in the particle size, even the packing having a particle size of about 5 $\mu$m, which is commonly used in the high-performance liquid chromatography, is very difficult to manufacture due to the limitation in view of the structure. Therefore, the pellicular-type ion exchanger cannot satisfy the requirement to have higher performance than the current theoretical plate number of 6,000 plates/column.

On the other hand, the porous chemical bond-type ion exchanger is excellent in the effective surface area of the packing because the ion migrates into pores to undertake the ion exchange. Therefore, this ion exchanger has a possibility of achieving higher performance. Although the porous chemical bond-type ion exchanger has a problem in that the peak is broadened due to the interference between the objective ion and the substrate, this broadening of the peak may be reduced by the manufacturing method described in JP-A-62-79356 (the term "JP-A" as used herein means an "unexamined published Japanese patent application"), where a spacer is introduced into the substrate and thereafter an ion exchange group is introduced. However, the porous chemical bond-type ion exchangers known at present cannot show sufficiently high alkali resistance at a pH of 9 or more and also lack the strength large enough to reduce the particle size and thereby achieve high performance.

In the analysis of anion using ion chromatography, the carbon dioxide gas contained in the sample is also detected as hydrogencarbonate ion. Therefore, in order to reduce the effect thereof to a minimum, a mixed aqueous solution of sodium carbonate and sodium hydrogencarbonate is widely used. However, in the analysis of trace components of a ppb level or less, hydrogencarbonate ion appears as a broad peak while overlapping with the peak of the objective ion to be analyzed and hence the objective ion is difficult to separate and quantitate. This broad peak appears as a recession or a projection from the base line depending on the concentration of the carbonate buffer solution used as the eluent and this recession or projection is called a carbonate dip or carbonate system peak (hereinafter referred to as a "carbonate dip").

The anion exchanger heretofore used mainly for the suppressor system column includes the above-described two kinds of ion exchangers, namely, a pellicular-type ion exchanger obtained by coating an anion exchangeable latex on a sulfonated polystyrene substrate and a porous chemical bond-type ion exchanger obtained by introducing an anion exchange group into a polyvinyl alcohol substrate. These two kinds of ion exchangers greatly differ in the hydrogencarbonate ion-holding ability because of the difference in the hydrophilicity of the substrate. However, whichever ion exchanger is used, a technique for manufacturing a column capable of controlling the appearance position of carbonate dip on the chromatogram has not yet been established. Thus, a problem arises at the time of microanalysis.

In order to avoid this problem, a manufacturing method of producing a copolymer of a styrene-type monomer having high hydrophobicity and an alcohol-type monomer having high hydrophilicity with controlling the ratio of each monomer mixed, thereby controlling the appearance position of carbonate dip, has been proposed as disclosed in JP-A-9-124729. However, the ion exchanger produced by this method shows a nitrate ion peak having a very bad shape with extreme tailing. The peak shape is evaluated based on the value (Fas) obtained by drawing a perpendicular line from the top of the chromatogram peak obtained, determining the horizontal widths in the right and in the left, respectively, of the peak from the perpendicular line at 10% of the peak height, and dividing the right width by the left width. In general, the chromatogram peak is almost bilaterally symmetric and accordingly, the Fas is in the vicinity of 1.0. However, in the case of the ion exchanger obtained by the method of the above-described publication, the Fas is 5.0 and by far larger. Thus, the quantitation of nitrate ion is not practical and the ion seeds eluting after the nitrate ion are also adversely affected. Therefore, this ion exchanger is not suitable for the microanalysis.

In the anion analysis using ion chromatography, it is ideal that the 7 standard inorganic anions be separated with a good balance in an analysis time as short as possible. However, fluoride ion is difficult to be held by the anion exchanger in the separation column and passes fast through the column. As a result, separation between the signal peak by the fluoride ion and water dip (negative peak appearing due to dilution of eluent by the injection of a sample) is insufficient so that the precision of quantitation tends to be deteriorated.

It would be advisable to use an eluent having a weak eluting power in order to increase with time in of fluoride ion. In this case, the elution time for divalent or more anions (sulfate ion and phosphate ion) is very long to make the analysis time redundant. In particular, where the eluent is alkaline, this problem is severe. For this reason, to simultaneously analyze fluoride ion and a divalent or more anion, the analysis conditions must be sophisticated.

Hence, a method for avoiding the above problems by optimization of the composition of eluent is being studied. For example, in the non-suppressor method, a method is proposed in which boric acid is added to the moving phase, which is weakly acidic and the boric acid and fluoride ion are allowed to selectively react to form an anionic compound, thereby increasing the holding ability as disclosed in JP-B-7-37972 (the term "JP-B" as used herein means an "examined Japanese patent publication") On the other hand, in the suppressor method, where a mixed solution of sodium carbonate and sodium hydrogencarbonate is used as an eluent, it has been known that varying the ratio of components can increase the holding ability of fluoride ion. Furthermore, a suppressor method in which a boric acid salt compound is added has been proposed as disclosed in JP-A-2000-180429. Thus, where the eluent can be constituted by a plurality of components, the above problems can be coped with by varying the composition thereof.

However, hydroxide base eluents such as aqueous sodium hydroxide solution and aqueous potassium hydroxide solution used as the eluent for a suppressor method are usually composed of a single component, so that the problems attributable to the eluent cannot be avoided. Therefore, in the suppressor method using such an alkaline eluent, a special technique must be used in order to make compatible the increase in the holding ability of fluoride ion and shortening of elution time for divalent or more anions (in particular phosphate ion among the 7 standard inorganic anions).

There have conventionally been practiced two methods. One is a gradient analysis method in which a concentration gradient is made in the eluent and another is a method in which the ion exchange capacity of the ion exchanger to be packed in the column is set to a greater value and a high concentration eluent as high as about 40 mM is used.

However, the first method is disadvantageous in that in order to impart the concentration gradient, it is necessary to provide at least two kinds of liquids having different concentrations and use an apparatus and operation for sucking and mixing them by means of two pumps and that a stabilization time during which the concentration of the eluent is returned to the original one for each measurement. The second method is disadvantageous in that because of the high concentration of eluent, the suppressor apparatus using an ion exchange membrane of a continuous regeneration type widely used at present requires application of high voltage for electrodialysis, which shortens the lifetime of suppressor.

When analyzing city water by a suppressor method using a hydroxide base eluent, not only improvement in the ability of holding fluoride ion and shortening of elution time for phosphate ion must be balanced but also sufficient separation of chloride ion and nitrite ion must be achieved at the same time. This is because in the analysis of city water, it is necessary to analyze nitrite ion on the order of several ppb in the presence of chloride ion on the order of several tens ppm. In the conventional column used for hydroxide base eluents, separation of chloride ion and nitrite ion is insufficient or carbonate ion is eluted during the separation if the separation is sufficient so that the analysis of trace amounts of nitrite ion is difficult to achieve at the same time.

Under the circumstances, a second object of the present invention is to provide a porous polymer particle for suppressor system ion chromatography, an anion exchanger comprising the particle, and a producing method thereof, where the particle is stable at high pH and favored with high-strength, which is capable of restricting elution time for phosphate ion to a short time on the order of from ten and several minutes to 30 minutes using a low concentration (for example, 20 mM or less) eluent without using gradient analysis, i.e., under isocratic conditions where the concentration is constant, sufficiently separating fluoride ion, which is difficult to hold, from water dip, and sufficiently separating chloride ion and nitrite ion to control the appearance position of carbonate dip not to overlap with the position of other ion peaks.

Further, a third object of the present invention is to provide a porous polymer particle in which a hydroxyl group or a carboxyl group is coexistent, an anion exchanger comprising the particle, and a producing method thereof, where in order to control the position of elution of each ion when anions are measured by a column for suppressor system or non-suppressor system ion analyzing chromatography for anion analysis, the particle is produced by introducing a quaternary ammonium group into a substrate which contains an ester bond as packing and treating with an alkaline solution to generate a hydroxyl group or a carboxyl group that can have negative charges repelling with the anions.

SUMMARY OF THE INVENTION

The present invention relates to the following porous polymer particle, anion exchanger for anion analyzing liquid chromatography, producing method thereof, packing material for anion chromatography, column for anion chromatography, and method for measuring anions.

1) A porous polymer particle comprising a polymer substrate having ester bonds, wherein a group containing a quaternary ammonium structure is connected to the substrate through a spacer molecule.

2) The porous polymer particle as described in 1) above, wherein the polymer substrate having ester bonds is (1) a polyvinyl alcohol substrate comprising a copolymer of a carboxylic acid vinyl ester and an isocyanurate-base crosslinking monomer, a part of the ester groups being saponified into a hydroxyl group or hydroxyl groups, (2) a substrate obtained by polymerizing one or more monomers selected from the group consisting of acrylate- and methacrylate-base crosslinking monomers each having a hydroxyl group, or (3) a substrate comprising a copolymer having a hydroxyl group obtained by saponifying a part of a copolymer of an alkanoyloxystyrene and divinylbenzene.

3) The porous polymer particle as described in 2) above, wherein the polymer substrate having an ester bond is a polyvinyl alcohol substrate comprising a copolymer of a carboxylic acid vinyl ester and an isocyanurate-base crosslinking monomer, a part of the ester groups being saponified into a hydroxyl group or hydroxyl groups.

4) The porous polymer particle as described in 2) above, wherein the polymer substrate having an ester bond is a substrate obtained by polymerizing one or more monomers selected from the group consisting of acrylate- and methacrylate-base crosslinking monomers each having a hydroxyl group.

5) The porous polymer particle as described in 2) above, wherein the polymer substrate having an ester bond is a substrate comprising a copolymer having a hydroxyl group obtained by saponifying a part of a copolymer of an alkanoyloxystyrene and divinylbenzene.

6) Alkali-resistant, high-strength porous polymer particle obtained by reacting a polyvinyl alcohol-base copolymer obtained by saponifying a part of the ester bonds in the copolymer of a carboxylic acid vinyl ester and an isocyanurate-base crosslinking monomer in an alkaline solution to convert into a hydroxyl group or hydroxyl groups, with a compound having two or more glycidyl groups in the molecule to introduce a glycidyl group-containing group such that the mass after the reaction is 103 to 140 assuming that the mass of the polyvinyl alcohol-base copolymer is 100 and then reacting the product with a nitrogen-containing compound that is derived into a group having a quaternary ammonium structure.

7) A porous polymer particle comprising an anion exchanger comprising a polymer substrate having an ester bond, treated with an alkaline solution to decompose the ester group to produce a hydroxyl group and/or a carboxyl group.

8) A porous polymer particle comprising a porous polymer or porous polymer particle comprising a polymer substrate having an ester bond to which a group having a quaternary ammonium structure is connected through a spacer molecule, the porous polymer or porous polymer particle being treated with an alkaline solution to decompose the ester group in the substrate to generate a hydroxyl group and/or a carboxyl group on a surface of the substrate.

9) The porous polymer particle as described in 7) or 8) above, wherein the polymer substrate having an ester bond is (1) a polyvinyl alcohol substrate comprising a copolymer of a carboxylic acid vinyl ester and an isocyanurate-base crosslinking monomer, a part of the ester groups being saponified into a hydroxyl group or hydroxyl groups, (2) a substrate obtained by polymerizing one or more monomers selected from the group consisting of acrylate- and methacrylate-base crosslinking monomers each having a hydroxyl group, or (3) a substrate comprising a copolymer having a hydroxyl group obtained by saponifying a part of a copolymer of an alkanoyloxystyrene and divinylbenzene.

10) The porous polymer particle as described in 1), 6) or 8) above, wherein the group containing a quaternary ammonium structure is derived from a group selected from trialkylamine, dialkylalkanolamine, N-alkyldialkanolamine, trialkanolamine, and aromatic or non-aromatic nitrogen-containing heterocyclic compounds.

11) A porous polymer particle comprising an alkali-resistant polymer substrate selected from a polyvinyl alcohol substrate comprising a copolymer of a carboxylic acid vinyl ester and an isocyanurate-base crosslinking monomer, a part of whose ester groups is saponified into a hydroxyl group or groups and a copolymer of alkanoyloxystyrene and divinylbenzene, a part of which is saponified to have a hydroxyl group or groups, wherein the substrate is connected with a group containing a quaternary ammonium structure derived from an aromatic or non-aromatic nitrogen-containing heterocyclic compound through a spacer molecule.

12) The porous polymer particle as described in 10) above, wherein the aromatic or non-aromatic nitrogen-containing heterocyclic compound is a compound selected from the group consisting of a pyridine compound represented by formula (1):

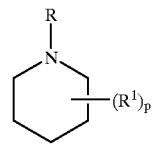

(1)

(wherein R represents an alkyl or alkoxy group having 1 to 5 carbon atoms, which is optionally substituted with a hydroxyl group or a halogen atom, or a halogen atom, and m is an integer of 0 to 5, provided that when m is 2 or more, plural R's may be the same or different), a 1-alkylpyrrolidine compound represented by formula (2):

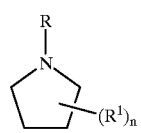

(2)

(wherein R represents an alkyl group having 1 to 5 carbon atoms, which is optionally substituted with a hydroxyl group or a halogen atom, $R^1$ represents a hydroxyl group or an alkyl group or alkoxy group having 1 to 5 carbon atoms, which is optionally substituted with a hydroxyl group, and n is an integer of 0 to 2), a 1-alkylpiperidine compound represented by formula (3):

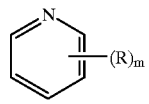

(3)

(wherein R represents an alkyl group having 1 to 5 carbon atoms, which is optionally substituted with a hydroxyl group or a halogen atom, $R^1$ represents a hydroxyl group or an alkyl group or alkoxy group having 1 to 5 carbon atoms, which is optionally substituted with a hydroxyl group, and p is an integer of 0 to 2), and a 1,4-dialkylpiperazine compound represented by formula (4):

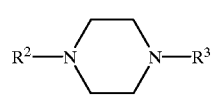

(4)

(wherein $R^2$ and $R^3$, which may be the same or different, independently represent a hydrogen atom, an alkyl group having 1 to 5 carbon atoms, which is optionally substituted with a hydroxyl group or a halogen atom, provided that $R^2$ and $R^3$ do not represent hydrogen atoms simultaneously).

13) The porous polymer particle as described in 1), 6), 7), 8) or 11) above, wherein the particle has a mean particle diameter of 1 to 30 μm.

14) The porous polymer particle as described in 1), 6), 7), 8) or 11) above, wherein the particle has a mean pore diameter of 50 to 300 Å.

15) An anion exchanger comprising the porous polymer particle as described in any one of 1) to 5), 7) to 10), and 12) to 14) above.

16) An alkali-resistant anion exchanger comprising the porous polymer particle as described in 6) or 11) above.

17) A method for producing an anion exchanger, comprising connecting a spacer molecule to a porous polymer particle comprising a polymer substrate having ester bonds and reacting the spacer molecule with a nitrogen-containing compound that is derived to a group having a quaternary ammonium structure to introduce an anion exchange group to the substrate.

18) The method for producing an anion exchanger as described in 17) above, wherein the polymer substrate having ester bonds is (1) a polyvinyl alcohol substrate comprising a copolymer of a carboxylic acid vinyl ester and an isocyanurate-base crosslinking monomer, a part of the ester groups being saponified into a hydroxyl group or hydroxyl groups, (2) a substrate obtained by polymerizing one or more monomers selected from the group consisting of acrylate- and methacrylate-base crosslinking monomers each having a hydroxyl group, or (3) a substrate comprising a copolymer having a hydroxyl group obtained by saponifying a part of a copolymer of an alkanoyloxystyrene and divinylbenzene.

19) The method for producing an anion exchanger as described in 18) above, wherein the polymer substrate having ester bonds is a polyvinyl alcohol substrate comprising a copolymer of a carboxylic acid vinyl ester and an isocyanurate-base crosslinking monomer, a part of the ester groups being saponified into a hydroxyl group or hydroxyl groups.

20) The method for producing an anion exchanger as described in 18) above, wherein the polymer substrate having ester bonds is a substrate obtained by polymerizing one or more monomers selected from the group consisting of acrylate- and methacrylate-base crosslinking monomers each having a hydroxyl group.

21) The method for producing an anion exchanger as described in 18) above, wherein the polymer substrate having ester bonds is a substrate comprising a copolymer having a hydroxyl group obtained by saponifying a part of a copolymer of an alkanoyloxystyrene and divinylbenzene.

22) A method for producing an alkali-resistant anion exchanger, comprising connecting a spacer molecule containing a glycidyl group to an alkali-resistant polymer porous particle selected from (1) a polyvinyl alcohol substrate comprising a copolymer of a carboxylic acid vinyl ester and an isocyanurate-base crosslinking monomer, a part of the ester groups being saponified into a hydroxyl group or hydroxyl groups, (2) a substrate obtained by polymerizing one or more monomers selected from the group consisting of acrylate- and methacrylate-base crosslinking monomers each having a hydroxyl group, and (3) a substrate comprising a copolymer having a hydroxyl group obtained by saponifying a part of a copolymer of an alkanoyloxystyrene and divinylbenzene through a bond that is not cleaved under an alkaline condition and reacting the glycidyl group with a nitrogen-containing compound that is derived to a group having a quaternary ammonium structure to introduce an anion exchange group into the substrate.

23) A method for producing an alkali-resistant, high-strength porous polymer particle, comprising reacting a polyvinyl alcohol-base copolymer obtained by saponifying a part of the ester bonds in the copolymer of a carboxylic acid vinyl ester and an isocyanurate-base crosslinking monomer in an alkaline solution to convert into a hydroxyl group or hydroxyl groups, with a compound having two or more glycidyl groups in the molecule to introduce a glycidyl group-containing group such that the mass after the reaction is 103 to 140 assuming that the mass of the polyvinyl alcohol-base copolymer is 100 and then reacting the product with a nitrogen-containing compound that is derived into a group having a quaternary ammonium structure.

24) A method for producing an anion exchanger, comprising treating an anion exchanger comprising a polymer substrate having an ester bond with an alkaline solution to decompose the ester group to produce a hydroxyl group and/or a carboxyl group on a surface of the substrate.

25) A method for producing an anion exchanger, comprising connecting a tertiary amine to a polymer substrate having ester bonds through a spacer molecule to obtain an anion exchanger comprising a porous polymer (particle) and treating the porous polymer or porous polymer particle with an alkaline solution to decompose the ester groups in the substrate to generate a hydroxyl group and/or a carboxyl group on a surface of the substrate.

26) The method for producing an anion exchanger as described in 24) or 25) above, wherein the polymer substrate having an ester bond is (1) a polyvinyl alcohol substrate comprising a copolymer of a carboxylic acid vinyl ester and an isocyanurate-base crosslinking monomer, a part of the ester groups being saponified into a hydroxyl group or hydroxyl groups, (2) a substrate obtained by polymerizing one or more monomers selected from the group consisting of acrylate- and methacrylate-base crosslinking monomers each having a hydroxyl group, or (3) a substrate comprising a copolymer having a hydroxyl group obtained by saponifying a part of a copolymer of an alkanoyloxystyrene and divinylbenzene.

27) The method for producing an anion exchanger as described in 17), 22), 24) or 25) above, wherein the group containing a quaternary ammonium structure is derived from a group selected from trialkylamine, dialkylalkanolamine, N-alkyldialkanolamine, trialkanolamine, and aromatic or non-aromatic nitrogen-containing heterocyclic compounds.

28) The method for producing an alkali-resistant high-strength anion exchanger as described in 23) above, wherein the saponification of the polyvinyl alcohol-base polymer is carried out until from 0.5 to 5 meq/g of a hydroxyl group is generated in the polymer.

29) The method for producing an alkali-resistant high-strength anion exchanger as described in 23) or 28) above, comprising treating in an alkaline solution.

30) The method for producing an alkali-resistant high-strength anion exchanger as described in 29) above, wherein a carbonic acid salt solution is used as the alkaline solution.

31) Packing material for ion chromatography comprising the anion exchanger as described in 15) or 16) above.

32) A column for ion chromatography having packed therein the anion exchanger as described in 15) or 16) above.

33) A column for suppressor system anion chromatography having packed therein the alkali-resistant anion exchanger as described in 16) above.

34) A method for measuring anions, comprising using the anion exchange-packed column as described in 32) or 33) above.

35) A method for measuring anions by a suppressor system anion chromatography, comprising using an alkaline eluent having a pH of 9 or more and the column for anion chromatography as described in 33) above.

36) The method for measuring anions by a suppressor system anion chromatography as described in 35) above, wherein at least one selected from the group consisting of carbonate buffer, borate buffer, aqueous sodium hydroxide solution, and aqueous potassium hydroxide solution is used as the alkaline eluent having a pH of 9 or more.

37) The method for measuring anions as described in 36) above, wherein 20 mM or less of the aqueous sodium hydroxide solution or aqueous potassium hydroxide solution is used as the alkaline eluent under an isocratic condition.

38) The method for measuring anions by suppressor system anion chromatography as described in any one of 35) to 37) above, further comprising adding an organic solvent in a ratio of 50 mass % or less to the alkaline eluent.

39) The method for measuring anions as described in 38) above, wherein acetone, acetonitrile or methanol is used as the organic solvent.

MODE FOR CARRYING OUT THE INVENTION

Figure 1:
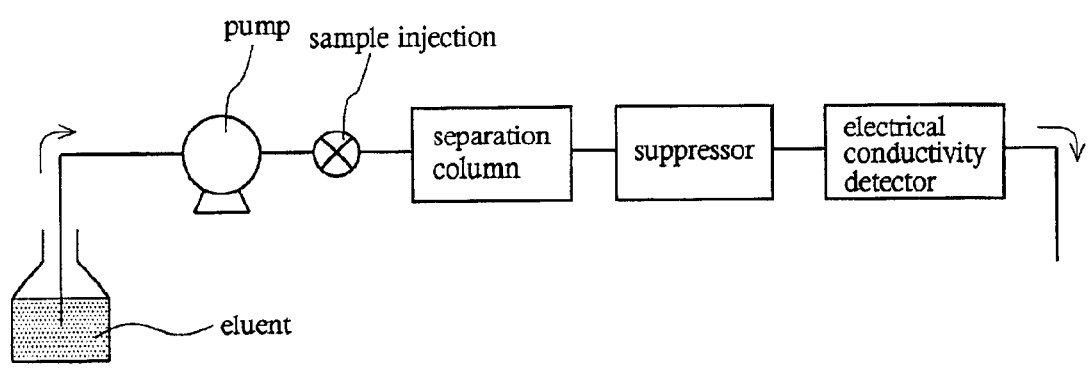
FIG. 1 shows a basic construction of ion chromatography.

First Embodiment:

A first embodiment of the present invention relates to a porous polymer particle comprising a polymer substrate having ester bonds, wherein a group containing a quaternary ammonium structure is connected to the substrate through a spacer molecule and an anion exchanger comprising the particle.

Here, the polymer substrate having ester bonds is (1) a polyvinyl alcohol substrate comprising a copolymer of a carboxylic acid vinyl ester and an isocyanurate-base crosslinking monomer, a part of the ester groups being saponified into a hydroxyl group or hydroxyl groups, (2) a substrate obtained by polymerizing one or more monomers selected from the group consisting of acrylate- and methacrylate-base crosslinking monomers each having a hydroxyl group, or (3) a substrate comprising a copolymer having a hydroxyl group obtained by saponifying a part of a copolymer of an alkanoyloxystyrene and divinylbenzene.

Suitable examples of isocyanurate-base crosslinking monomer used in the polyvinyl alcohol substrate comprising a copolymer of a carboxylic acid vinyl ester and an isocyanurate-base crosslinking monomer, a part of the ester groups being saponified into a hydroxyl group or hydroxyl groups as described in (1) above include cross-linking monomers having an isocyanurate ring represented by the following formula (5):

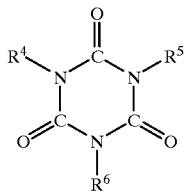

(5)

—$CH_2$—C≡CH or —$CH_2$—C($CH_3$)=$CH_2$. Among these, triallylcyanurate where $R^4$, $R^5$ and $R^6$ all are —$CH_2CH$=$CH_2$ is preferred as a cross-linking agent because of its good copolymerizability with vinyl acetate and high stability against the saponification.

In the produce of a polyvinyl alcohol-type copolymer, a method of reacting a cross-linking agent with wholly porous polyvinyl alcohol particles is generally used. For example, a porosity-imparting agent such as butyl acetate, and a radical polymerization initiator are added to divinyl adipate and the mixture is suspension-polymerized in water and then reacted in methanol to produce a hydroxyl group, thereby obtaining polyvinyl alcohol particles. Thereafter, the polyvinyl alcohol is reacted and cross-linked with epichlorohydrin in a solution containing acetone and dimethyl sulfoxide to obtain a desired substrate.

The crosslinking monomer for the substrate obtained by polymerizing one or more monomers selected from the group consisting of acrylate- and methacrylate-base crosslinking monomers each having a hydroxyl group as described in (2) above includes glycerol diacrylate, glycerol dimethacrylate, pentaerythritol diacrylate, pentaerythritol dimethacrylate, pentaerythritol triacrylate, pentaerythritol trimethacrylate, sorbitol diacrylate, sorbitol dimethacrylate and the like. Among these it is particularly preferred to use glycerol dimethacrylate solely.

The one or more monomers selected from the group consisting of acrylate- and methacrylate-base crosslinking monomers each having a hydroxyl group are aqueous suspension-polymerized to convert it into a crosslinked gel.

The aqueous suspension polymerization is to perform suspension polymerization in an aqueous medium. The aqueous medium comprises water as an essential component and its weight ratio to the monomer is preferably from 300 to 1,000% by weight and more preferably from 400 to 800% by weight.

The polymerization is carried out in the presence of a polymerization initiator. The polymerization initiator which can be used includes organic peroxides such as benzoyl peroxide, dichlorobenzoyl peroxide, dicumyl peroxide, 2,5-di(peroxybenozate)hexyne-3, 1,3-bis(tertbutylperoxyisopropyl)benzene, lauroyl peroxide, tert-butyl peracetate, 2,5-dimethyl-2,5-di(tert-butylperoxy)hexyne-3, 2,5-dimethyl-2,5-di(tert-butylperoxy)hexane, tert-butyl perbenzoate, and methyl ethyl ketone peroxide and azo-base compounds such as 2,2'-azobis(2,4-dimethylvaleronitrile). Among these, 2,2'-azobis(2,4-dimethylvaleronitrile) is used preferably.

The amount of polymerization initiator to be used is determined depending on the kind of monomer and the like and the initiator is used in an amount of usually from 0.1 to 4.0% by weight based on the weight of the monomer.

In the present invention, in order not to inhibit the stability of the suspension system, a suitable water-soluble polymer is used as a dispersant and further an inorganic acid salt is used as a dispersion auxiliary. The water-soluble polymer includes gelatin, starch, CMC(carboxymethylcellulose), polyvinyl alcohol, polyvinyl alcohol partial saponificate, vinyl alcohol copolymer, polyacrylic acid and the like. Among these, polyvinyl alcohol is used preferably.

Further, the dispersion auxiliary includes sodium chloride, potassium chloride, sodium sulfate and the like and preferred is sodium chloride.

By addition of a suitable diluent to the monomer phase at the time of polymerization, porous crosslinked polymer particles can be obtained. Rendering the crosslinked polymer particles porous results in an increase in the amount of functional groups which can be introduced, so that the performance of the particle as a carrier for anion analyzing chromatography can be improved.

The diluent to be used includes toluene, diethylbenzene, n-hexane, n-dodecane, n-hexanol, cyclohexanol, octanol, dodecanol, propyl acetate, butyl acetate and the like. Among these, n-hexanol is used preferably. The diluents may be used singly or two or more in admixture. The diluent is used in an amount of 0 to 200% by weight based on the weight of the monomer. If the amount of the diluent is small, it is difficult to obtain a porous polymer while if the amount of the diluent is too large, the resulting polymer tends to have a porosity that is too large to prevent a decrease in mechanical strength.

It is advisable to perform the polymerization reaction usually at a temperature of from 60 to 90° C. for approximately from 6 to 10 hours.

The crosslinked gel obtained by the polymerization preferably comprises spherical particles having a particle diameter of from 1 to 50 μm, preferably from 2 to 20 μm and more preferably 3 to 10 μm, which may be classified before they can be used, if desired.

In the substrate comprising a copolymer having a hydroxyl group obtained by saponifying a part of a copolymer of an alkanoyloxystyrene and divinylbenzene as described in (3) above, alkanoyloxystyrene includes, for example, acetoxystyrene and the like.

In order to facilitate the introduction of quaternary ammonium groups to the polymer substrate having ester bonds described in (1) to (3) above, or to attain a good separation in an anion analysis, an epoxy group is introduced to the hydroxyl groups that the substrate has through a spacer such as epichlorohydrin, ethylene glycol diglycidyl ether or ester, 1,4-butanediol diglycidyl ether or ester, or polyethylene glycol diglycidyl ether or ester, and then a quaternary ammonium group is introduced. Among the spacers, 1,4-butanediol diglycidyl ether is used preferably. Then, in order to introduce a group containing a quaternary ammonium structure, a compound selected from trialkylamine, dialkylalkanolamine, N-alkyldialkanolamine, trialkanolamine, and aromatic or non-aromatic nitrogen-containing heterocyclic compounds is reacted to obtain crosslinked polymer particles for anion analyzing liquid chromatography.

Here, the trialkylamine includes, for example, trimethylamine, tributylamine, triethylamine, tripropylamine and the like. The dialkylalkanolamine includes 2-dimethyl-aminoethanol, 2-diethylaminoethanol and the like. The N-alkyldialkanolamine includes N-methyldiethanolamine, N-ethyldiethanolamine and the like. The trialkanolamine includes triethanolamine, triisopropanolamine and the like.

Further, the aromatic or non-aromatic nitrogen-containing heterocyclic compound includes a compound selected from the group consisting of a pyridine compound represented by formula (1):

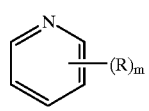

(1)

(wherein R represents an alkyl or alkoxy group having 1 to 5 carbon atoms, which is optionally substituted with a hydroxyl group or a halogen atom, or a halogen atom, and m is an integer of 0 to 5, provided that when m is 2 or more, plural R's may be the same or different), a 1-alkylpyrrolidine compound represented by formula (2):

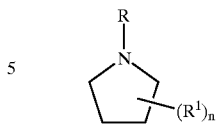

(2)

(wherein R represents an alkyl group having 1 to 5 carbon atoms, which is optionally substituted with a hydroxyl group or a halogen atom, $R^1$ represents a hydroxyl group or an alkyl group or alkoxy group having 1 to 5 carbon atoms, which is optionally substituted with a hydroxyl group, and n is an integer of 0 to 2), a 1-alkylpiperidine compound represented by formula (3):

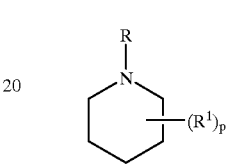

(3)

(wherein R represents an alkyl group having 1 to 5 carbon atoms, which is optionally substituted with a hydroxyl group or a halogen atom, $R^1$ represents a hydroxyl group or an alkyl group or alkoxy group having 1 to 5 carbon atoms, which is optionally substituted with a hydroxyl group, and p is an integer of 0 to 2), and a 1,4-dialkylpiperazine compound represented by formula (4):

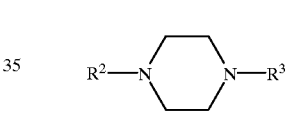

(4)

(wherein $R^2$ and $R^3$, which may be the same or different, independently represent a hydrogen atom, an alkyl group having 1 to 5 carbon atoms, which is optionally substituted with a hydroxyl group or a halogen atom, provided that $R^2$ and $R^3$ do not represent hydrogen atoms simultaneously).

Specific examples thereof include pyridine, 2-methylpyridine, 3-methylpyridine, 4-methylpyridine, 2-hydroxy-4-methylpyridine, 2-hydroxy-6-methylpyridine, 2-hydroxypyridine, 3-hydroxypyridine, 4-hydroxypyridine, 1-methylpyrrolidine, 1-ethylpyrrolidine, 1-methylpiperidine, 1-ethylpiperidine, 1-(2-hydroxethyl) piperidine, 1-(hydroxymethyl)-piperidine, 1-(2-hydroxyethyl)pyrrolidine, 2-(2-hydroxyethyl)-1-methylpyrrolidine, 3-hydroxy-3-methylpiperidine, 4-hydroxy-1-methylpiperidine, 4-chloro-1-methylpiperidine, 1-(2-chloroethyl)piperidine, 1-(2-chloroethyl)pyrrolidine, 1-methylpiperazine, 1-ethylpiperazine, or 1,4-dimethylpiperazine.

According to the first embodiment of the present invention, a group containing a quaternally ammonium structure is introduced to the porous polymer particle substrate having ester bonds through a spacer to obtain crosslinked polymer particles for anion analyzing liquid chromatography having high mechanical strength.

The crosslinked polymer particles for anion analyzing liquid chromatography obtained by the present invention have a small particle diameter and high mechanical strength and hence a column for anion analyzing liquid chromatography using the particles has excellent separation performance and is useful for high-sensitivity anion measurement in anion chromatography.

Second Embodiment:

A second embodiment of the present invention relates to a porous polymer particle that is useful as an alkali-resistant, high-strength anion exchanger obtained by reacting a polyvinyl alcohol-base copolymer obtained by saponifying a part of the ester bonds in the copolymer of a carboxylic acid vinyl ester and an isocyanurate-base crosslinking monomer in an alkaline solution to convert into a hydroxyl group or hydroxyl groups, with a compound (spacer molecule) having two or more glycidyl groups in the molecule to introduce a glycidyl group-containing group such that the mass after the reaction is 103 to 140 assuming that the mass of the polyvinyl alcohol-base copolymer is 100 and then reacting the product with a nitrogen-containing compound that is derived into a group having a quaternary ammonium structure as well as to an alkali-resistant and high-strength anion exchanger comprising the particles.

Suitable examples of the isocyanurate-type cross-linking monomer which can be used in the present invention include cross-linking monomers having a isocyanurate ring represented by the following formula (5):

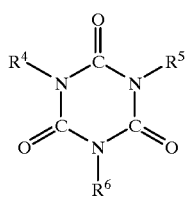

(5)

wherein the symbols have the same meanings as defined above. Among these, triallylcyanurate corresponding to the formula (5) where $R^4$, $R^5$ and $R^6$ all are —$CH_2CH=CH_2$ is preferred as a cross-linking agent because of its good copolymerizability with vinyl acetate and high stability against the saponification.

In the produce of a polyvinyl alcohol-type copolymer, a method of reacting a cross-linking agent with wholly porous polyvinyl alcohol particles is generally used. For example, a porosity-imparting agent such as butyl acetate, and a radical polymerization initiator are added to divinyl adipate and the mixture is suspension-polymerized in water and then reacted in methanol to produce a hydroxyl group, thereby obtaining polyvinyl alcohol particles. Thereafter, the polyvinyl alcohol is reacted and cross-linked with epichlorohydrin in a solution containing acetone and dimethyl sulfoxide to obtain a desired substrate.

However, in order to obtain a substrate having higher strength, a method of saponifying a copolymer of a carboxylic acid vinyl ester and a cross-linking monomer having an isocyanurate ring to convert a part of the ester groups in the copolymer into a hydroxyl group (see, JP-B-63-61619) may be used. In the present invention, the anion exchanger having high-strength and alkali-resistance is obtained using a method of saponifying a copolymer of a carboxylic acid vinyl ester and a cross-linking monomer having an isocyanurate ring represented by formula (5) to convert a part of the ester groups in the copolymer into a hydroxyl group. In this method, the hydroxyl group has a role of elevating the hydrophilicity of the substrate and inhibiting the interference with ion and at the same time plays a part as an active site necessary for the reaction with a glycidyl compound which is one constituent component of the present invention.

In the present invention, for sufficiently introducing the glycidyl group-containing group, the saponification is preferably performed to a hydroxyl group density of 0.5 to 5 meq/g. After the saponification, the hydroxyl group is preferably present in a density of 1.0 to 3 meq/g. If the hydroxyl group density is less than 0.5 meq/g, the necessary glycidyl group-containing group is disadvantageously difficult to introduce, whereas if the saponification is performed to exceed 5 meq/g, the strength of the substrate decreases, therefore, the particle size of the substrate cannot be reduced to improve the performance and this is not preferred.

The term "carboxylic acid vinyl ester" as used in the present invention means a compound having one or more polymerizable carboxylic acid vinyl ester group. Examples thereof include vinyl acetate, vinyl propionate, vinyl butyrate, vinyl valerate and vinyl pivalate. These are used individually or in combination of two or more thereof. Among these, preferred are vinyl acetate and vinyl propionate which are relatively hydrophilic and facilitated in the polymerization and saponification.

In the present invention, for obtaining a copolymer comprising a cross-linking monomer, an ordinary polymerization method such as suspension polymerization, bulk polymerization and emulsion polymerization, may be used.

In the present invention, the glycidyl group-containing group introduced into the polyvinyl alcohol-base copolymer is a group capable of acting as a spacer for introducing a so-called ion exchange group, and thereby exhibiting a function of elongating the distance between the substrate and the ion exchange group, preventing the interference between the ion and the substrate and inhibiting the diffusion of the peak.

Examples of the reagent for introducing the glycidyl group-containing group include epichlorohydrin, 1,4-butanediol diglycidyl ether, ethylene glycol diglycidyl ether and glycerin diglycidyl ether. In order to obtain the alkali-resistant anion exchanger of the present invention, a compound containing two or more glycidyl groups in the same molecule, such as 1,4-butanediol diglycidyl ether, must be reacted.

An increase in mass after the reaction with the glycidyl compound is from 103 to 140 assuming that the mass of the polyvinyl alcohol is 100. If the increase in mass is less than 103, insufficient alkali resistance disadvantageously results, whereas if it exceeds 140, the particle may become soft or the particles may be associated with each other, and this is not preferred. The increase in mass after the reaction with the glycidyl compound is preferably from 104 to 135, more preferably from 105 to 125.

As the glycidyl group-containing group for use in the present invention, for example, a group represented by formula (6) is used.

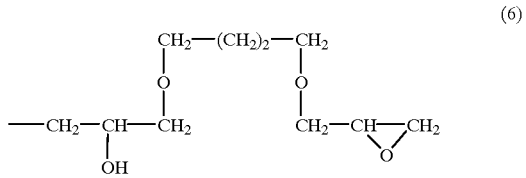

(6)

In the present invention, the compound to be reacted with the glycidyl group-containing group for introducing the quaternary ammonium structure may include the same compounds as described above with respect to the first embodiment of the present invention.

As specific examples thereof, there can be utilized tertiary amines such as trimethylamine, triethylamine, tributylamine, diethylethanolamine, N-ethyldiethanolamine, 1-methylpiperidine, 1-methylpyrrolidine, pyridine and methylpyridine may be used. These tertiary amines differ from each other in the reactivity and also in the selectivity of ion that is intended to separate. Generally, a tertiary amine having good reactivity and capable of eluting the ion as much as possible within a short time is selected. In the present invention, trimethylamine, diethylethanolamine, 1-methylpiperidine, and 1-methylpyrrolidine are preferred, with 1-methylpiperidine and 1-methylpyrrolidine being particularly preferred.

The anion exchanger of the present invention can be obtained by the above-described producing methods, but the present invention is not limited to these producing methods.

In another embodiment, the method for producing an anion exchanger according to the present invention is characterized in that a known anion exchanger is reacted in an alkaline solution to change the affinity of the substrate for the hydrogencarbonate ion, whereby the ion exchange capacity and the hydrophilicity of the substrate can be freely controlled so as to elute the carbonate dip at the position not overlapping with other anion peaks.

Examples of the alkaline solution which can be used in the present invention include a single or mixed solution of a hydroxide such as sodium hydroxide and potassium hydroxide, or a carbonate such as sodium hydrogencarbonate, sodium carbonate, potassium hydrogencarbonate or potassium carbonate.

The reaction is usually performed in an alkaline solution of 0.1 to 10 M at a temperature of 50° C. to 120° C. approximately for 1 to 40 hours, however, it is also possible to set the concentration of the alkaline solution, the reaction temperature or the reaction time out of these normal ranges.

The anion exchanger used for the modification is not particularly limited. In the present invention, the above-described alkali-resistant high-strength anion exchanger is used.

The anion exchanger obtained in the present invention suitably has a particle diameter of from 1 to 30 $\mu$m, preferably from 2 to 20 $\mu$m, more preferably from 2 to 10 $\mu$m. If the particle diameter of the anion exchanger exceeds 30 $\mu$m, the theoretical plate number of the column disadvantageously decreases, whereas if the particle size is less than 1 $\mu$m, the column pressure excessively elevates and the filling becomes extremely difficult. Therefore, this is not preferred.

In the present invention, the particle diameter is measured by a Coulter Counter.

The anion exchanger obtained by the present invention is a porous polymer particle and the pore diameter is controlled using a method commonly used for the packing for high performance liquid chromatography. The pore diameter of the porous polymer particle is from 50 to 300 Å, preferably from 50 to 150 Å, more preferably from 50 to 100 Å. If the pore diameter of the porous polymer particle is less than 50 Å, the surface area is small and the glycidyl group-containing group is difficult to introduce. Therefore, this is not preferred. On the other hand, if it exceeds 300 Å, the strength of the particle disadvantageously decreases.

The pore diameter can be determined by the technique described in J. Chromedogr. 387 (1987) 65 of reverse size exclusion chromatography, a BET (Brunauer-Emmett-Teller) method, or the like. In the present invention, pore diameter is measured according to the method described in Angw. Chem. Int. Ed. Engl., 17, 901–908 (1987), unless there is a problem specially.

Upon the measurement, first the particles to be measured are filled in a column, which then is connected to an HPLC apparatus and plural standard polystyrenes over a wide range of molecular weight and benzene are each measured of retention volume (ml) using THF (tetrahydrofuran) as an eluent. The results obtained are plotted on a graph calibrated by molecular weight M on Y-axis (use of logarithmic graduation will be helpful for viewing at a sight) vs. retention volume (ml) on X-axis. The curve smoothly connecting the plotted points thus obtained is called a calibration curve. From the calibration curve, exclusion bound ($V_1$, $M_1$) are obtained by a conventional method. Using these points and measured points of benzene ($V_2$, 78), a line $X=(V_1+V_2)/2$ is plotted on a graph. Then, the coordinate Y, $M_m$, of the intersection of this straight line and calibration curve (hereinafter called "mean pore point") is read and this value is introduced into the following equation (X) to calculate a mean pore point $\phi_m$ (Å)

$$\phi_m = 0.62 \times (M_m)^{0.59} \tag{X}$$

The "mean pore point" above is defined by the present inventors and means the point at which the accumulated volume from the minimum volume (the size in which benzene is just fitted in) is 50%, assuming the total pore volume is 100%. The above equation is used for converting the standard polystyrene equivalent molecular weight at this point to the diameter of a pore in which the standard polystyrene is just fitted in.

The anion exchanger obtained in the present invention is filled into a column in accordance with a known filling method such as slurry method, to provide an alkali-resistant and high-sensitive column for suppressor system ion chromatography.

The column using the anion exchanger of the present invention is stable against the eluent used in the suppressor system ion chromatography. Particularly, the column is stable also when the eluent having a pH of 9 to 12 used in the alkali side is at least one selected from the group consisting of a carbonate buffer, a borate buffer, an aqueous sodium hydroxide solution and an aqueous potassium hydroxide solution.

The column using the anion exchanger of the present invention can also be used by adding an organic solvent to the eluent in a concentration of 50 mass % or less and in this case, the elution time of hydrophobic anion may be reduced or the separation balance among respective ions may be easily controlled.

The organic solvent used is not particularly limited as long as it is a solvent commonly used in the eluent for suppressor system ion chromatography. Examples thereof include acetone, acetonitrile, methanol, ethanol, isopropanol, glycerol and tetrahydrofuran. Among these, acetone, acetonitrile, methanol and the like are preferred.

The column filled with the anion exchanger of the present invention can attain good separation of main inorganic anions such as phosphate ion, fluoride ion, chloride ion, nitrite ion, bromide ion, nitrate ion and sulfate ion, and organic acid ions such as acetate ion, formate ion, methacrylate ion and oxalate ion, by appropriately selecting the exchange capacity of the ion exchanger and the concentration of the eluent.

Examples of the use of the column for suppressor system ion chromatography of the present invention include analysis of trace components in the environment such as air (trace sour gas, acid rain and the like), water (river water, tap water, spa water, limnetic water, drainage, and the like) and soil (anions in soil extract solution and the like); analysis of food, such as analysis of $BrO_3$ ion in bread; analysis of $PO_4$ ion, fertilizer or the like in plant; analysis of anion in cosmetic starting material; analysis of anion in coating raw material, coating material or surface finishing solution; analysis of ultrapure water, mixed acid, air, lead frame, wafer or the like in the semiconductor field; quality control in the pharmaceutical field; and analysis of circulating water, cooling water or the like at the electric power plant.

Furthermore, the column for suppressor system ion chromatography of the present invention has a high theoretical plate number as compared with conventional columns and can separate even a component that cannot be heretofore separated. Therefore, the column is not limited to the above-described uses. Also, the column may be used in the electric material producing process for which high-sensitive analysis is required, even under the isocratic eluent conditions ready for the control of pollution in a clean room by organic acids such as acetic acid and formic acid, for the analysis of components contained in semiconductor washing or for the analysis of methacrylic acid or the like dissolved out from adhesives.

The anion exchanger and the column for suppressor system ion chromatography according to the second embodiment of the present invention have sufficiently high alkali resistance against the eluent used in the suppressor system ion chromatography. Furthermore, since the anion exchanger has high-strength and can be reduced in the particle size, the column using the anion exchanger can attain a theoretical plate number as high as twice or more the theoretical plate number of conventional anion exchange columns for ion chromatography.

By using the producing method of the anion exchanger of the present invention, an anion analysis column for suppressor system ion chromatography can be produced, which can freely control the carbonate dip position. When this column is used, the effect of the carbonate dip can be eliminated at the analysis of trace components, so that the separation/quantification of the objective ion can be easily performed.

The column for suppressor system ion chromatography, packed with the anion exchanger of the present invention can restrict the elution time of phosphate ion in 20 minutes under isocratic conditions using a low concentration hydroxide-base eluent of 20 mM or less, sufficiently separate fluoride ion, which is difficult to retain, from water dip and sufficiently separate chloride ion and nitrite ion, so that it can shorten the measurement time in the analysis using the above eluent and prolong the lifetime of continuous-type and regeneration-type ion exchanger membrane suppressor.

Accordingly, the present invention is useful in the fields over the wide range, such as environment, food, agriculture, cosmetics, coating material, semiconductor, medicament and electric power. It is particularly useful in the case where analysis of several ppb nitrite ion in the presence of several tens ppm chloride ion is required as in city water analysis.

Third Embodiment:

A third embodiment of the present invention relates to a porous polymer particle capable of controlling retention time of anions obtained treating a substrate including ester bonds, which have been used as an anion exchanger, with an alkaline solution to decompose the ester group to produce a hydroxyl group and/or a carboxyl group on the surface of the substrate and to an anion exchanger comprising the particle.

In the anion exchanger of the present invention, the substrate for anion exchanger having the effect of controlling the retention time of anions is (1) a polyvinyl alcohol substrate comprising a copolymer of a carboxylic acid vinyl ester and an isocyanurate-base crosslinking monomer, a part of the ester groups being saponified into a hydroxyl group or hydroxyl groups, (2) a substrate obtained by polymerizing one or more monomers selected from the group consisting of acrylate- and methacrylate-base crosslinking monomers each having a hydroxyl group, or (3) a substrate comprising a copolymer having a hydroxyl group obtained by saponifying a part of a copolymer of an alkanoyloxystyrene and divinylbenzene Treatment of the substrates (1) to (3) above with an alkali solution after introducing a quaternary ammonium group therein through a spacer to convert it to anion exchanger can generate a hydroxyl group on the surface of a vinyl ester-base substrate and a carboxyl group and a hydroxyl group on the surfaces of acrylate-base and methacrylate-base substrates, respectively.

Here, the hydroxyl group generated is dissociated in an alkaline eluent to be charged negatively while the carboxyl group is dissociated in a weakly acidic to alkaline eluent. Therefore, upon analyzing anions by a column using the packing, there occurs repelling action with the negative charge that the anion has so that the retention time of anions can be controlled.

The carboxylic acid vinyl ester-base monomer used for forming a substrate in the present invention includes vinyl acetate, vinyl formate and the like. The substrate prepared by copolymerization of the monomer and a crosslinking monomer is subjected to hydrolysis to convert a part of the ester bonds on the surface of the substrate to hydroxyl groups, to which a spacer is introduced, through which a tertiary amine or a nitrogen-containing heterocyclic compound is reacted to thereby introduce a quaternary ammonium group.

The acrylate- and methacrylate-base crosslinking monomers having a hydroxyl group include glycerol diacrylate, glycerol dimethacrylate, pentaerythritol diacrylate, pentaerythritol dimethacrylate, pentaerythritol acrylate, pentaerythritol methacrylate, sorbitol diacrylate, sorbitol dimethacrylate and the like. A spacer is introduced to the hydroxyl groups on a surface of the substrate prepared by polymerization of one or more selected from the crosslinking monomers or copolymerization with other crosslinking agent and through this tertiary amine is reacted to introduce a quaternary ammonium group.

In the third embodiment of the present invention, specific examples of the substrate having ester bonds, which are used preferably, include a polyvinyl alcohol comprising a copolymer of a carboxylic acid vinyl ester and an isocyanurate-base crosslinking monomer, a part of the ester groups being saponified into a hydroxyl group or hydroxyl groups, a (co)polymer obtained by polymerizing one or more monomers selected from the group consisting of acrylate- and methacrylate-base crosslinking monomers each having a hydroxyl group, a copolymer having a hydroxyl group obtained by saponifying a part of a copolymer of an alkanoyloxystyrene (for example, acetoxystyrene) and divinylbenzene, and the like.

The spacer molecule used in the present invention comprises a plurality of atoms, usually 3 atoms or more between the surface of the substrate and the ion exchange group. The spacer connects on one hand with the alkali-resistant porous polymer and on the other hand with the ion exchange group. As a result, it serves as a spacer that extends the distance between them and has the function of preventing the interference between the ion and the substrate to inhibit the diffusion of the peak.

As the spacer molecule, there can be used compounds containing a glycidyl group that connects with a nitrogen-containing compound that is derived into a group having a quaternary ammonium structure, for example, epichlorohydrin, 1,4-butanediol diglycidyl ether, ethylene glycol diglycidyl ether, glycerol diglycidyl ether, and the like. Where alkali-resistant, high-strength anion exchanger for suppressor methods is to be produced, compounds having two or more glycidyl groups in the molecule are used.

As the tertiary amine or aromatic or non-aromatic nitrogen-containing heterocyclic compound to be reacted with the glycidyl group of the substrate for introducing a quaternary ammonium group, there can be used the same compounds as previously described with respect to the second embodiment of the present invention. Specific examples thereof include trimethylamine, triethylamine, tributylamine, diethanolamine, N-ethyl-diethanolamine, 1-methylpiperidine, 1-methylpyrrolidine, pyridine, methylpyridines. Among these, 1-methylpyrrolidine is used preferably.

The alkaline solution which can be used for subjecting the ester groups of the above anion exchanger to alkali treatment to hydrolyze it include a single or mixed solution of a hydroxide such as sodium hydroxide and potassium hydroxide, or a carbonate such as sodium hydrogencarbonate, sodium carbonate, potassium hydrogencarbonate or potassium carbonate.

The reaction is performed usually in an about 0.1 to about 10 M alkaline solution at from about 50° C. to about 120° C. for about 1 to about 40 hours. However, the concentration of the alkaline solution, reaction temperature and reaction time may be set outside the usual ranges.

The anion exchanger obtained in the present invention suitably has a particle diameter of from 1 to 30 μm, preferably from 2 to 20 μm, more preferably from 2 to 10 μm. If the particle diameter of the anion exchanger exceeds 30 μm, the theoretical plate number of the column disadvantageously decreases, whereas if the particle size is less than 1 μm, the column pressure excessively elevates and the filling becomes extremely difficult.

The anion exchanger obtained by the present invention is a porous polymer particle and the pore diameter is controlled using a method commonly used for the packing for high performance liquid chromatography. The pore diameter of the porous polymer particle is from 50 to 300 Å, preferably from 50 to 150 Å, more preferably from 50 to 100 Å. If the pore diameter of the porous polymer particle is less than 50 Å, the surface area is small and the glycidyl group-containing group is difficult to introduce. Therefore, this is not preferred. On the other hand, if it exceeds 300 Å, the strength of the particle disadvantageously decreases.

The particulate anion exchanger obtained in the present invention is used as packing for a column for suppressor system or non-suppressor system ion chromatography.

The filling of anion exchanger into a column is performed in accordance with a known filling method such as a slurry method to provide an alkali-resistant and high-sensitive column for anion chromatography.

The column using the anion exchanger of the present invention is stable against the eluent used in the suppressor system or non-suppressor system ion chromatography since in the anion exchanger, the ester bonds that have been present on a position where they are prone to decomposition on the surface of the substrate are decomposed in advance by the alkali treatment. Therefore, the column has stable performance.

BEST MODE FOR CARRYING OUT THE INVENTION

Hereinafter, the present invention will be described in detail by examples. However, they are merely exemplary and the present invention should not be construed as being limited thereto.

EXAMPLE 1 (MA-base Polymer+Spacer)

In a 300 ml beaker, 100 g of glycerol dimethacrylate, 50 g of n-hexyl alcohol, and 1.5 g of 2,2'-azobis (isobutyronitrile) were weighed and the mixture was subjected to an ultrasonic treatment for 2 minutes in an ultrasonic cleaner and further was mixed for 10 minutes with a stirrer. The mixture was transferred into a 1 l-volume reactor for homogenizing, and 333 ml of aqueous 2% polyvinyl alcohol (KURARAY POVAL PVA-224 manufactured by KURARAY CO., LTD.) and 2% NaCl solution were added. The mixture was stirred for 40 minutes at room temperature using a homogenizer. Then, this was transferred into a reactor equipped with a stirrer and the temperature controller was set to 63° C. (external temperature) and heated as was for 6 hours or more to obtain crosslinked gel that was insoluble in water and organic solvents. The gel was centrifuged and the precipitates were collected, washed with 500 ml of water and with 500 ml of ethanol, air-dried, and then classified by air classification to obtain particles of from 3 to 6 μm in particle diameter. To introduce a spacer to 20 g of the crosslinked gel particles by the reaction mechanism shown by the following Scheme (A), 40 g of 1N NaOH aqueous solution and 40 g of 1,4-butanediol diglycidyl ether were weighed in an eggplant-shaped flask and were allowed to react at 30° C. for 3 hours with stirring to obtain 1,4-butanediol diglycidyl ether-modified crosslinked polymer particles. The particles were washed with 100 ml of water and with 100 ml of acetone, and then air-dried.

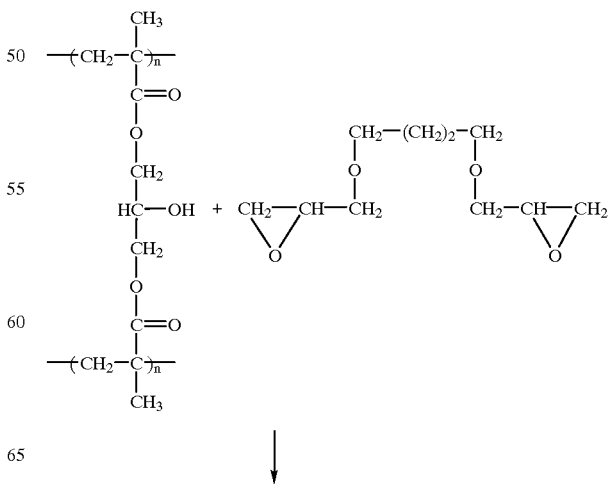

Scheme (A)

-continued

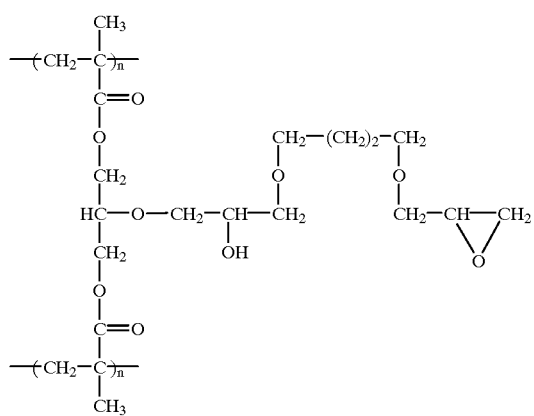

To convert the resulting 1,4-butanediol diglycidyl ether-modified crosslinked polymer particles to a quaternary ammonium salt by the reaction mechanism shown by the following Scheme (B), 10 g of the 1, 4-butanediol diglycidyl ether-modified crosslinked polymer particles, 45 g of 1,4-dioxane, and 7.5 g of N-methylpiperidine were weighed in an eggplant-shaped flask and were allowed to react at 35° C. for 1 hour with stirring to obtain quaternary ammonium-converted crosslinked polymer particles. The particles were washed twice with 100 ml of acetone, once with 100 ml of water, once with 100 ml of 0.5N HCl, once with 100 ml of water, twice with 100 ml of 0.1N NaOH and three times with 100 ml of water.

Scheme (B)

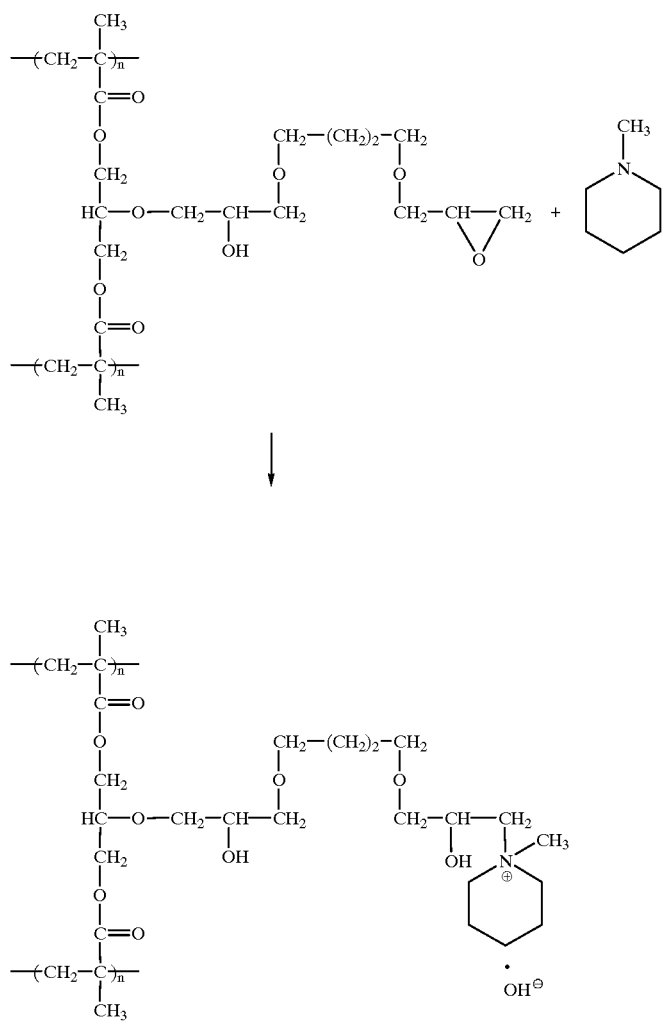

Figure 2:
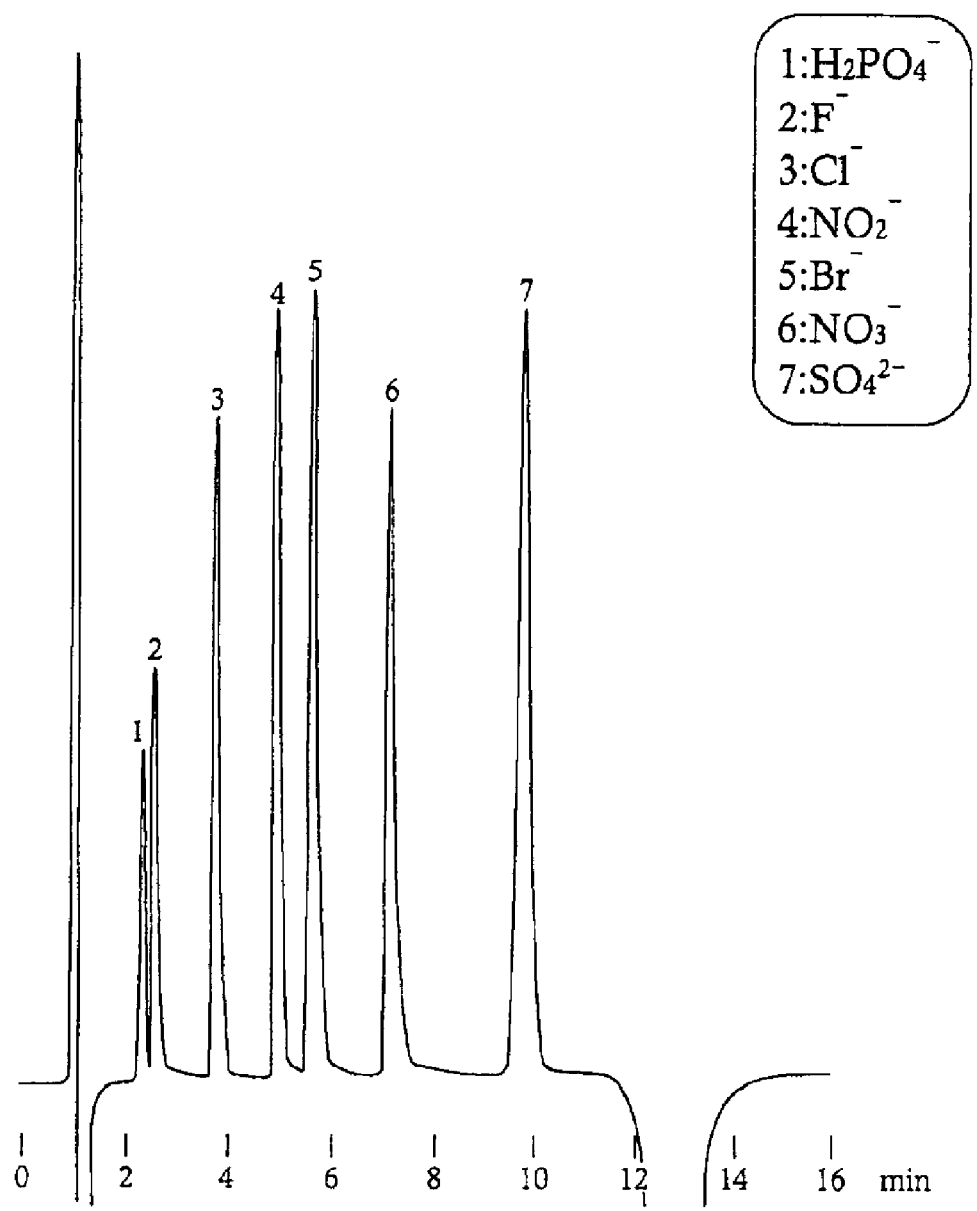
FIG. 2 is a separation chromatogram obtained in Example 1.

The crosslinked polymer particles obtained by the above means were filled in a stainless column of 4.6 mm in diameter×100 mm in length as a chemical bond-type ion exchanger made of crosslinked polymer particles for anion analyzing liquid chromatography to fabricate a column for anion analyzing liquid chromatography. 50 μl of an aqueous solution containing 20 mg/l phosphate ion, 1.5 mg/l fluoride ion, 2.5 mg/l chloride ion, 6 mg/l nitrite ion, 10 mg/l bromide ion, 10 mg/l nitrate ion, and 10 mg/l sulfate ion was injected as a sample and evaluation of column was performed to obtain a chromatogram as shown in FIG. 2.

In FIG. 2, theoretical plate number for each ion was 4,200 plates/10 cm for phosphate ion, 3,800 plates/10 cm for fluoride ion, 7,100 plates/10 cm for chloride ion, 7,600 plates/10 cm for nitrite ion, 7,000 plates/10 cm for bromide ion, 7,000 plates/10 cm for nitrate ion, and 7,600 plates/10 cm for sulfate ion.

COMPARATIVE EXAMPLE 1

Figure 3:
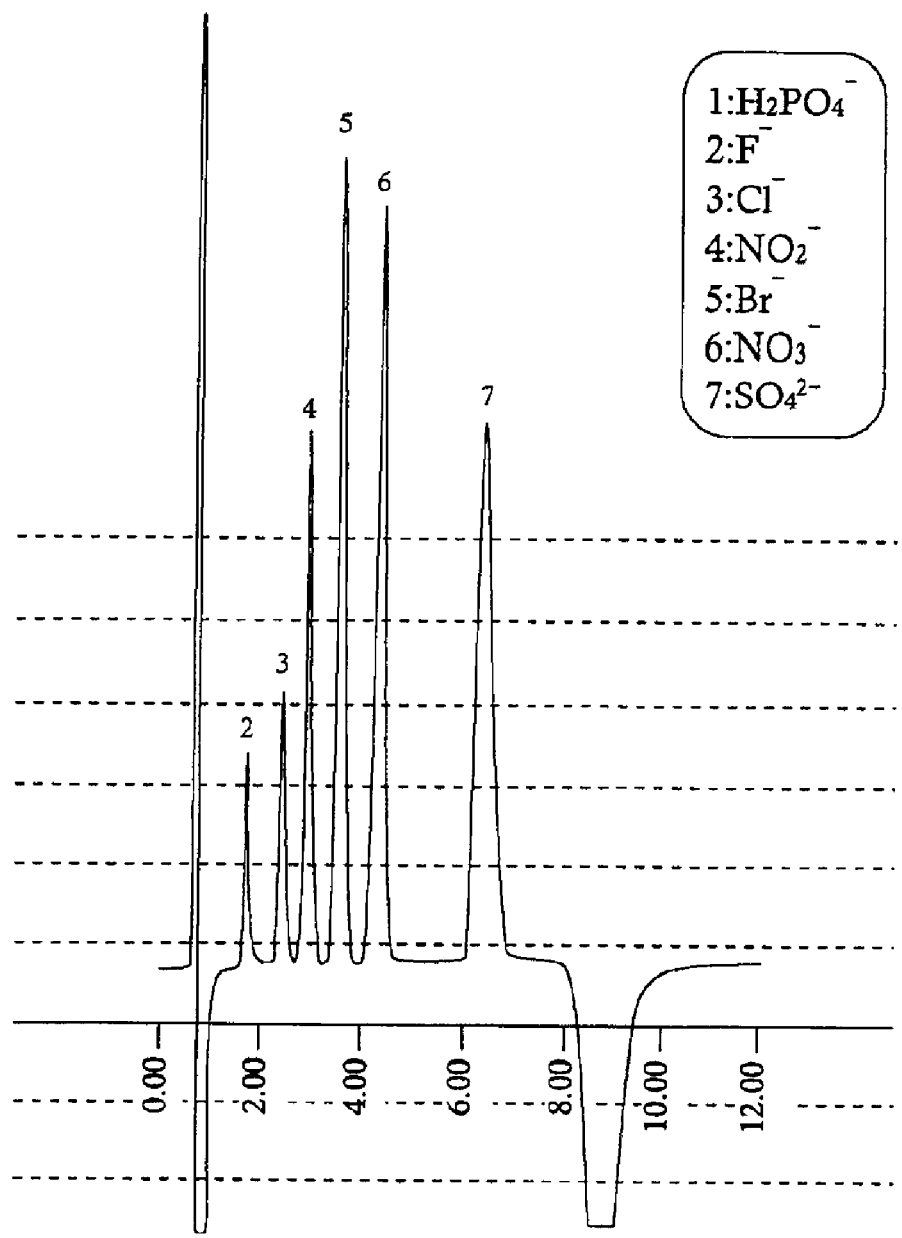
FIG. 3 is a separation chromatogram obtained in Comparative Example 1.

Using Shodex (registered trademark: SHOWA DENKO K.K.) IC I-524A as the separation column, measurement was performed under the same conditions as in Example 1. FIG. 3 shows the obtained chromatogram.

In FIG. 3, the theoretical plate number for nitrate ion was 3,000 plates/10 cm.

EXAMPLE 2

A uniformly mixed solution containing 100 g of vinyl acetate, 180 g of triallyl isocyanurate, 150 g of butyl acetate and 10 g of 2,2'-azobis(isobutyronitrile), and 1,400 ml of water having dissolved therein a small amount of polyvinyl alcohol and sodium phosphate were charged into a 5 l-volume three-neck flask equipped with a reflux condenser and the resulting mixed solution was stirred for 10 minutes. Subsequently, while stirring under nitrogen stream, polymerization was performed at 60° C. for 16 hours to obtain a particulate polymer. This polymer was filtrated, washed, extracted with acetone, dried, charged together with 3 l of caustic soda into a 5 l-volume three-neck flask equipped with a reflux condenser, a nitrogen inlet tube and a stirrer, and saponified while stirring at 15° C. for 20 hours under nitrogen stream. The resulting polymer was again filtered, washed and dried. In the polyvinyl alcohol copolymer obtained by the saponification, the density of hydroxyl group was 2.1 meq/g. Using this as a substrate, an anion exchanger was produced through the following procedure.

Into 2 l-volume three-neck flask equipped with a nitrogen inlet tube and a stirrer, 100 g of the dry polymer obtained above, 50 g of 1,4-butanediol diglycidyl ether (hereinafter referred to as "1,4-BGE") and 1,000 ml of dimethyl sulfoxide were charged. The resulting mixture was stirred at 35° C. for 16 hours under nitrogen stream to introduce a glycidyl group-containing group into the polymer substrate. After the introduction, the polymer was washed with dimethyl sulfoxide and water and then dried by a vacuum dryer. The mass of the dried polymer was 104 g and thus, the increment from the original substrate was 4%.

Into a 2 l-volume three-neck flask equipped with a nitrogen inlet tube and a stirrer, 100 g of the polymer having introduced thereinto a glycidyl group-containing group, 60 ml of a 1% aqueous triethylamine solution and 1,000 ml of water were charged. The resulting solution was stirred at 50° C. for 4 hours under nitrogen stream to introduce an amine group, thereby preparing an anion exchanger. This anion exchanger was washed with methanol, 1N hydrochloric acid and 1N caustic soda, by providing intervention of water washing between respective washing operations. Thereafter, the anion exchanger was immersed in 0.5 M sodium carbonate and treated at 60° C. for 5 hours, followed by water washing and drying. The thus-obtained anion exchanger had a particle diameter of 5 μm and an ion exchange capacity of about 50 μeq/g.

The anion exchanger obtained above was filled in a polyether ether ketone resin (PEEK)-made column having an inside diameter of 4.6 mm and a length of 150 mm to prepare an anion exchange column.

Using MIC-20 (manufactured by Metrohm Ltd.) equipped with a suppressor as the ion chromatograph, 30 μl of an aqueous solution containing 2 mg/l of $F^-$, 5 mg/l of $Cl^-$, 10 mg/l of $NO_2^-$, 10 mg/l of $Br^-$, 10 mg/l of $NO_3^-$, 10 mg/l of $PO_4^{3-}$ and 10 mg/l of $SO_4^{2-}$ was injected as a standard solution into the ion chromatograph while passing though 3 mM sodium carbonate as the eluent at 1.0 ml/min.

Figure 4:
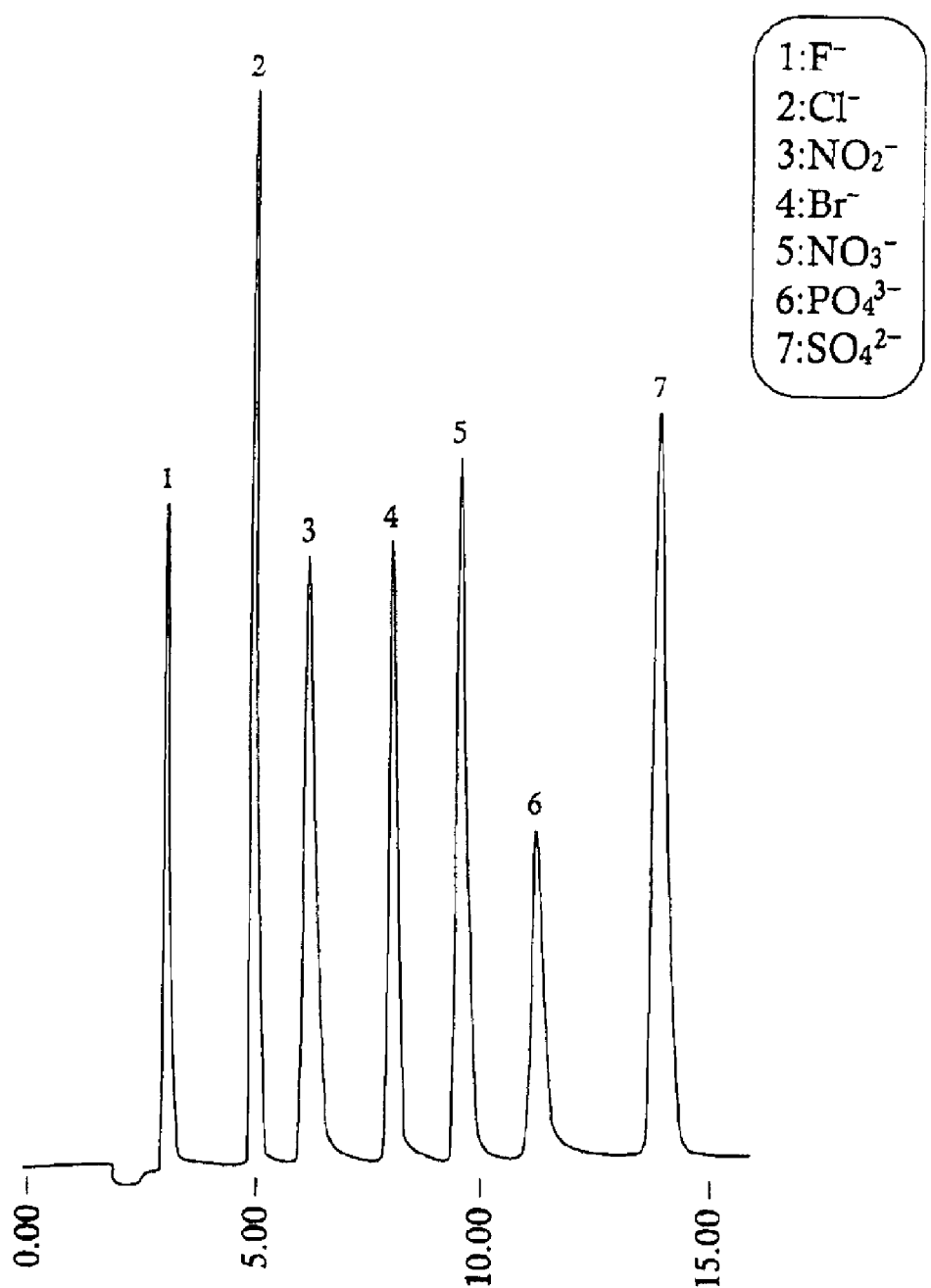
FIG. 4 is a chromatogram on the standard liquid (aqueous solution containing 2 mg/l $F^-$, 5 mg/l $Cl^-$, 10 mg/l $NO_2^-$, 10 mg/l $Br^-$, 10 mg/l $NO_3^-$, 10 mg/l $PO_4^{3-}$, and 10 mg/l $SO_4^{2-}$) by the ion exchanger-packed column of the present invention obtained in Example 2.

FIG. 4 shows the chromatogram obtained. The theoretical plate number of this column was calculated from the peak of $SO_4^{2-}$ ion and found to be 12,000 plates.

This was as high as about two times as compared with commercially available pellicular system ion exchange columns now being used most widely.

In order to examine the durability of this column, the chromatogram was recorded by continuously passing the above-described eluent at 1.0 mg/l and injecting the above-described standard solution at regular intervals to monitor the change in the column performance. When the eluent was passed for 500 hours, the fluctuation in the retention time of each ion was from 2 to 3% so that sufficiently high practical utility was revealed.

EXAMPLE 3

Into a 2 l-volume three-neck flask equipped with a nitrogen inlet tube and a stirrer, 100 g of the polyvinyl alcohol polymer prepared in Example 2 was charged as the substrate together with 100 g of 1, 4-BGE and 1,000 ml of dimethyl sulfoxide. The resulting mixture was stirred at 35° C. for 16 hours under nitrogen stream to introduce a glycidyl group-containing group into the polymer substrate. After the introduction, the polymer was washed with dimethyl sulfoxide and water, and then dried by a vacuum dryer. The mass of the dried polymer was 108 g, thus, the increment from the original substrate was 8%.

According to the same formulation as in Example 2, 100 g of the polymer having introduced thereinto a glycidyl group-containing group prepared above was aminated. The anion exchanger obtained (ion exchange capacity: 50 μeq/g) was filled into the same column as used in Example 2. The thus-obtained separation column had a theoretical plate number ($SO_4^{2-}$) of 11,500 and in the eluent passing test for 500 hours, almost no fluctuation occurred in the retention time of each ion. Therefore, good durability was revealed.

EXAMPLE 4

Figure 6:
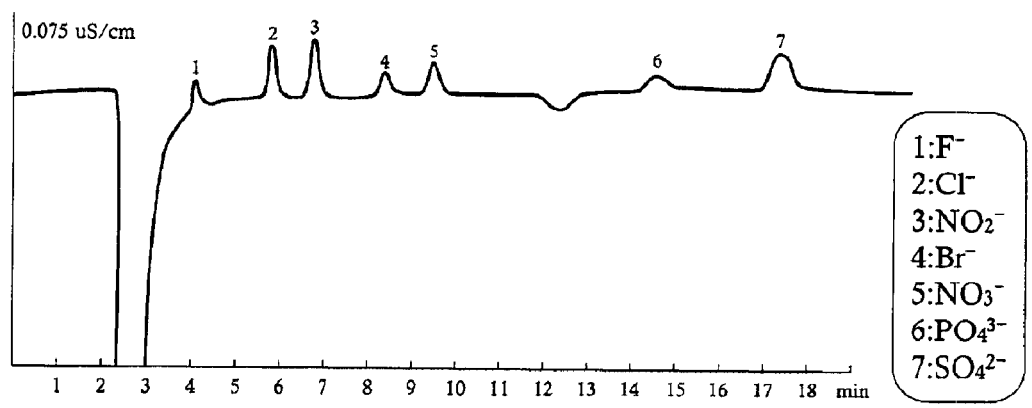
FIG. 6 is a chromatogram of an aqueous solution containing $F^-$ (2 μg/l), $Cl^-$ (3 μg/l), $NO_2^-$ (5 μg/l), $Br^-$ (10 μg/l), $NO_3^-$ (10 μg/l), $PO_4^{3-}$ (15 μg/l), $SO_4^{2-}$ (15 μg/l) by the column of Example 4.

An anion exchanger was prepared according to the same formulation as in Example 2 except for changing the amount of 1,4-BGE to 450 g, and using this, an anion exchange column was manufactured. The increment due to the introduction of a glycidyl group-containing group was 35%. Using this column, a chromatogram was collected, after injecting 100 μl of an aqueous solution containing 2 μg/l of $F^-$ ion, 3 μg/l of $Cl^-$ ion, 5 μg/l of $NO_2^-$ ion, 10 μg/l of $Br^-$ ion, 10 μg/l of $NO_3^-$ ion, 15 μg/l of $PO_4^3$ ion and 15 μg/l of $SO_4^{2-}$ ion. FIG. 6 shows the obtained chromatogram.

The thus-obtained column had a theoretical plate number ($SO_4^{2-}$) of 12,000 and in the eluent passing test for 500 hours, almost no fluctuation occurred in the retention time of each ion.

EXAMPLE 5

An anion exchanger was prepared according to the same formulation as in Example 2 except for using 300 g of glycerol diglycidyl ether (hereinafter referred to as "GDE") as a reagent for the introduction of a glycidyl group-containing group and performing the reaction for 6 hours. Using this, an anion exchange column was manufactured. The increment due to the introduction of a glycidyl group-containing group was 25%, the theoretical plate number ($SO_4^{2-}$) of the column obtained was 10,500 and in the eluent passing test for 500 hours, almost no fluctuation occurred in the retention time.

COMPARATIVE EXAMPLE 2

An anion exchanger was prepared according to the same formulation as in Example 2 except for changing the amount of 1,4-BGE to 20 g, and using this, an anion exchange column was manufactured. The increment due to the introduction of a glycidyl group-containing group was 2%, the theoretical plate number ($SO_4^{2-}$) of the column obtained was 12,000. In the eluent passing test for 500 hours, the fluctuation in the retention time was 50%. Thus, this anion exchange column had no practical utility as a suppressor system anion column.

COMPARATIVE EXAMPLE 3

An anion exchanger was prepared according to the same formulation as in Example 2 except for changing the amount of 1,4-BGE to 550 g, and using this, an anion exchange column was manufactured. The increment due to the introduction of a glycidyl group-containing group was 45%. However, association of anion exchanger particles with each other occurred and the theoretical plate number of the packed anion exchange column was 1,500 ($SO_4^{2-}$). Thus, this column had no practical utility as a suppressor system anion column.

COMPARATIVE EXAMPLE 4

An anion exchanger was prepared according to the same formulation as in Example 2 except for using 50 g of epichlorohydrin (hereinafter referred to as "EPCH") as a reagent for the introduction of a glycidyl group-containing group, and using this, an anion exchange column was manufactured. The increment due to the introduction of a glycidyl group-containing group was 5% and the theoretical plate number ($SO_4^{2-}$) of the anion exchange column obtained was 12,500. However, when this column was subjected to an eluent passing test for 500 hours, the fluctuation in the retention time of each ion was 70%. Thus, this anion exchange column had no practical utility as a suppressor system anion column.

COMPARATIVE EXAMPLE 5

An anion exchanger was prepared according to the same formulation as in Example 2 except for using 200 g of EPCH as a reagent for the introduction of a glycidyl group-containing group, and using this, an anion exchange column was manufactured. The increment due to the introduction of a glycidyl group-containing group was 15% and the theoretical plate number ($SO_4^{2-}$) of the anion exchange column obtained was 12,500. However, when this column was subjected to an eluent passing test for 500 hours, the fluctuation in the retention time of each ion was 70%. Thus, this anion exchange column had no practical utility as a suppressor system anion column.

The kind and amount of the reagent for the introduction of a glycidyl group-containing group, the increment (%) due to the introduction of a glycidyl group-containing group, the theoretical plate number of the column, the results of fluctuation in the retention time of each ion when the eluent (3.5 mM $Na_2CO_3$) was passed for 500 hours, which were used and obtained in Examples 2 to 5 and Comparative Examples 2 to 5, are shown in Table 1.

TABLE 1

| | Amount of Glycidyl Group-Containing Group Introduced | | Theoretical Plate Number of Column | Fluctuation of Retention Time at the Passing of Eluent for 500 Hours |
|---|---|---|---|---|
| Reagent | Amount Used (g) | Amount Introduced (mass %) | | |
| Example 2 | 1,4-BGE | 50 g | 4% | 12,000 | 2 to 3% |
| Example 3 | 1,4-BGE | 100 g | 8% | 11,500 | almost none |
| Example 4 | 1,4-BGE | 450 g | 35% | 12,000 | almost none |
| Example 5 | GDE | 300 g | 25% | 10,500 | almost none |
| Comparative Example 2 | 1,4-BGE | 20 g | 2% | 12,000 | 50% |
| Comparative Example 3 | 1,4-BGE | 550 g | 45% | 1,500 | — |
| Comparative Example 4 | EPCH | 50 g | 5% | 12,500 | 70% |
| Comparative Example 5 | EPCH | 200 g | 15% | 12,500 | 70% |

It is seen that the column for ion chromatography using the anion exchanger of the present invention exhibits a theoretical plate number as high as about twice that of conventional columns and has sufficiently high durability against the passing of the eluent used in the suppressor system ion chromatography.

EXAMPLE 6

Preparation of Anion Exchanger

Into a 2 l-volume three-neck flask equipped with a nitrogen inlet tube and a stirrer, 100 g of the polyvinyl alcohol polymer prepared in Example 2 was charged as a substrate together with 300 g of 1,4-BGE and 1,000 ml of dimethyl sulfoxide. The resulting mixture was stirred at 35° C. for 12 hours under nitrogen stream to introduce a glycidyl group-containing group into the polymer substrate. After the introduction, the polymer was washed with dimethyl sulfoxide and water and then dried by a vacuum dryer. The mass of the dried polymer was 110 g, thus, the increment from the original substrate was 10%.

According to the same formulation as in Example 3, 100 g of the polymer having introduced thereinto a glycidyl group-containing group was aminated, and using this, an anion exchanger was produced.

Alkali Treatment

Into a 2 l-volume three-neck flask equipped with a stirrer, 100 g of the anion exchanger prepared above and 1,000 ml of 1M sodium carbonate were charged and treated at 98° C. for from 1 to 6 hours, followed by washing and drying, so as to modify the exchanger into various kinds of anion exchangers different in the appearance position of the carbonate dip.

EXAMPLE 7

2.0 g of each anion exchanger prepared in Example 6 was dispersed in 10 ml of an aqueous 0.5M sodium chloride solution and filled under pressure into a polyether ether ketone resin (PEEK)-made column having an inside diameter of 4.6 mm and a length of 250 mm to manufacture an anion exchanger column.

The anion exchange columns manufactured above each was installed to anion chromatograph and as an eluent, a mixed aqueous solution of 1.8 mM sodium carbonate and 1.7 mM sodium hydrogencarbonate was passed at 1.0 ml/min.

As a sample, 20 µl of an aqueous solution containing 2 mg/l of $F^-$ ion, 3 mg/l of $Cl^-$ ion, 5 mg/l of $NO_2^-$ ion, 10 mg/l of $Br^-$ ion, 10 mg/l of $NO_3^-$ ion, 15 mg/l of $PO_4^{3-}$ ion and 15 mg/l of $SO_4^{2-}$ ion was injected.

Figure 5:
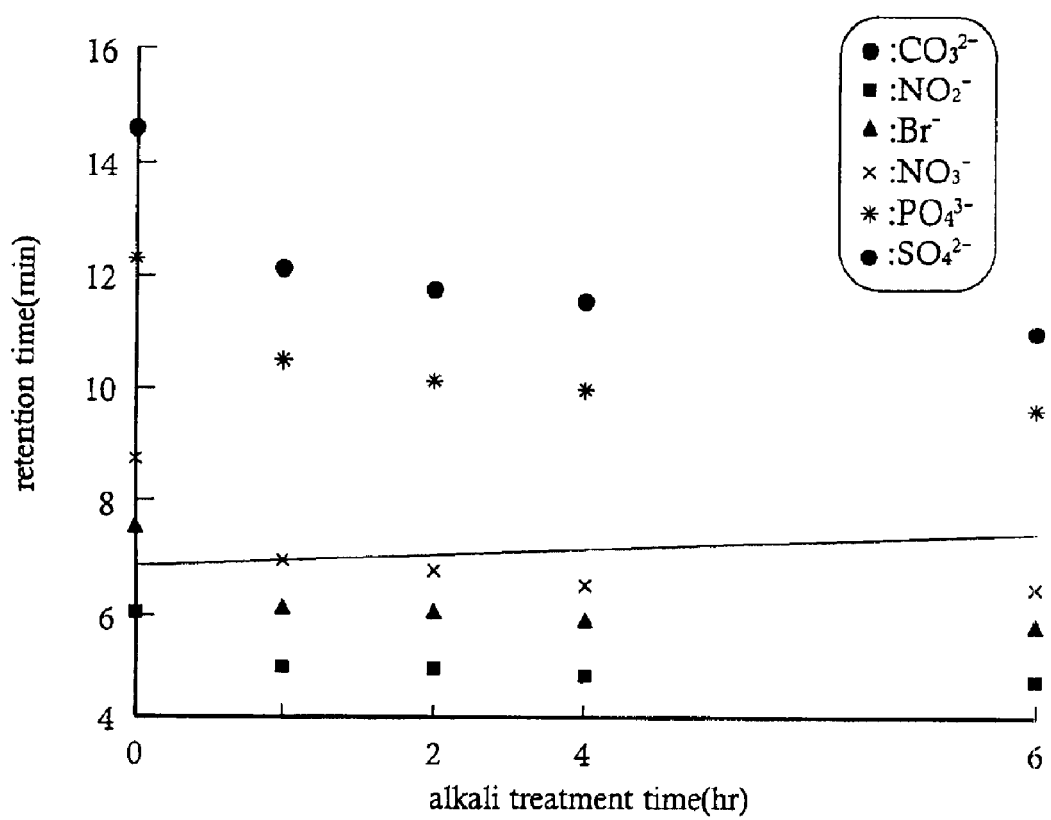
FIG. 5 is a chromatogram showing the relationship between the alkali treatment time and the anion retention time or the carbonate dip appearance position, obtained using the column of Example 7.

FIG. 5 shows the comparison of the retention time among various ions, obtained from the chromatograph of each column.

As shown in FIG. 5, when an alkali treatment is performed, the retention time of various anions becomes shorter, however, since the appearance position of the carbonate dip comes out later, it can be seen that the appearance position of the carbonate dip can be controlled by controlling the alkali treatment conditions.

EXAMPLE 8

As the substrate resin to which an ion exchange group was to be introduced, a polyvinyl alcohol-base polymer prepared by the following method was used. That is, a uniformly mixed solution containing 100 g of vinyl acetate, 180 g of triallyl isocyanurate, 150 g of butyl acetate and 10 g of 2,2'-azobis(isobutyronitrile), and 1,400 ml of water having dissolved therein a small amount of polyvinyl alcohol and sodium phosphate were charged into a 5 l-volume three-neck flask equipped with a reflux condenser and the resulting mixed solution was stirred for 10 minutes. Subsequently, while stirring under nitrogen stream, polymerization was performed at 60° C. for 16 hours to obtain a particulate polymer. This polymer was filtrated, washed, extracted with acetone, and then dried.

The obtained polymer was charged together with 3 l of 1N aqueous sodium hydroxide (NaOH) into a 5 l-volume three-neck flask equipped with a reflux condenser, a nitrogen inlet tube and a stirrer, and saponified while stirring at 15° C. for 20 hours under nitrogen stream. The resulting polymer was again filtered, washed and dried. In the polyvinyl alcohol copolymer obtained by the saponification, the density of hydroxyl group was 2.1 meq/g. Using this as a substrate, an anion exchanger was manufactured through the following procedure Into 1 l-volume three-neck flask equipped with a nitrogen inlet tube and a stirrer, 100 g of the dry polymer obtained above, 300 g of 1,4-BGE, 300 ml of dimethyl sulfoxide, and 65 ml of aqueous 30% by weight sodium hydroxide solution were charged. The resulting mixture was stirred at 35° C. for 12 hours under nitrogen stream to introduce a glycidyl group-containing group into the polymer substrate. After the introduction, the polymer was washed with dimethyl sulfoxide and with water and then dried by a vacuum dryer. The mass of the dried polymer was 110 g and thus, the increment from the original substrate was 10%.

Into a 1 l-volume three-neck flask equipped with a nitrogen inlet tube and a stirrer, 100 g of the polymer having introduced thereinto a glycidyl group-containing group, 4 g of 1-methylpiperidine, and 500 ml of water were charged. The resulting solution was stirred at 40° C. for 1 hour under nitrogen stream to introduce a tertiary heterocyclic amine group, thereby preparing an anion exchanger. This anion exchanger was washed with 1N hydrochloric acid and with 1N aqueous sodium hydroxide solution, by providing intervention of water washing between respective washing operations. Thereafter, the anion exchanger was immersed in 1N aqueous sodium hydroxide solution and treated at 60° C. for 5 hours, followed by water washing and drying. The thus-obtained anion exchanger had a mean particle diameter of 5 µm and an ion exchange capacity of about 20 µeq/g.

Figure 7:
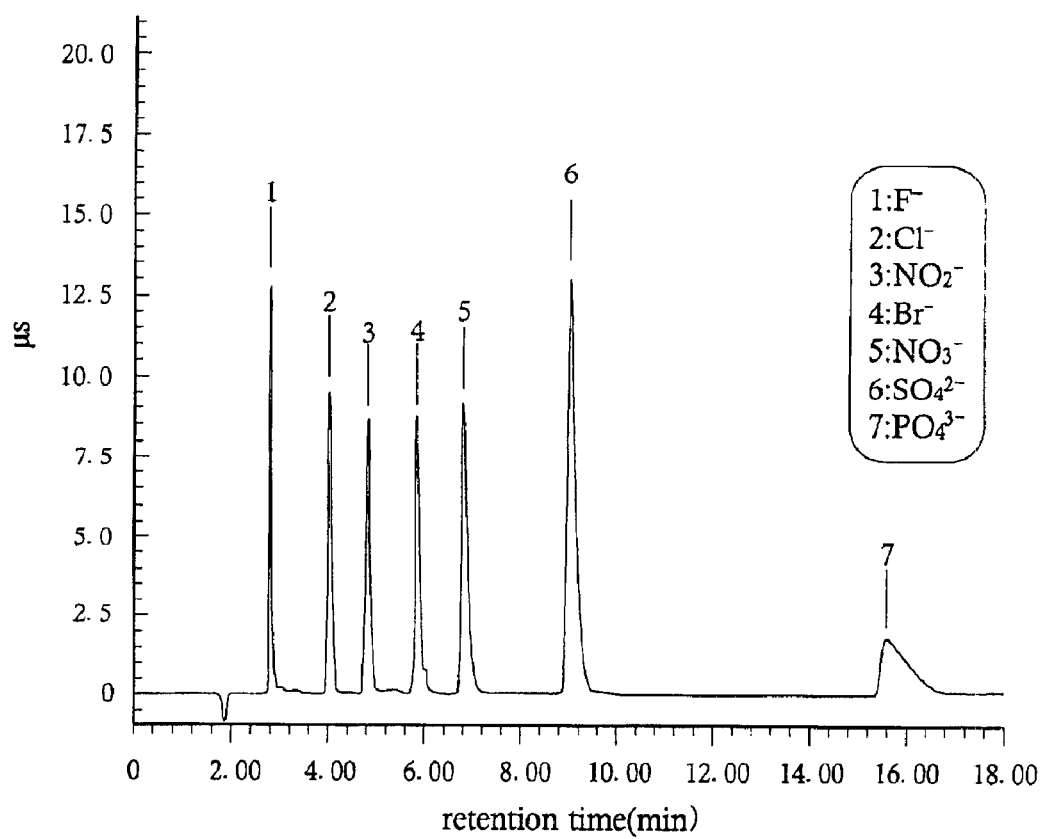
FIG. 7 is a chromatogram obtained by injecting a test aqueous solution containing 7 standard ions in a separation column obtained by packing the ion exchanger of the present invention obtained in Example 8.

The anion exchanger was filled in a polyether ether ketone resin (PEEK)-made column having an inside diameter of 4.0 mm and a length of 250 mm to prepare an anion exchange column. Using DX-320 (manufactured by Dionex Corporation) equipped with a suppressor as the ion chromatograph, 15 mM aqueous sodium hydroxide solution as the eluent was passed at 1.0 ml/min and 25 µl of an aqueous solution containing 2 mg/l of $F^-$, 3 mg/l of $Cl^-$, 5 mg/l of $NO_2^-$, 10 mg/l of $Br^-$, 10 mg/l of $NO_3^-$, 15 mg/l of $SO_4^{2-}$, and 15 mg/l of $PO_4^{3-}$ and was injected as a standard solution into the ion chromatograph at a column temperature of 35° C. FIG. 7 shows the chromatogram obtained.

EXAMPLE 9

1,4-BGE was introduced to the polyvinyl alcohol-base resin prepared in Example 8 as a substrate in the same formulation as in Example 8.

100 g of the polymer having introduced therein to a glycidyl group-containing group, 10 g of 1-methylpyrrolidine, and 500 ml of water were charged in a 1 l-volume three-neck flask equipped with a nitrogen inlet tube and a stirrer and stirred at 40° C. for 1 hour to introduce tertiary heterocyclic amine to the substrate to prepare an anion exchanger. This was washed with 1N hydrochloric acid and with 1N aqueous sodium hydroxide solution by providing intervention of water washing between respective washing operations. Thereafter, the anion exchanger was immersed in a 1N aqueous sodium hydroxide solution and treated at 60° C. for 5 hours, followed by water washing and drying. The thus-obtained anion exchanger had a mean particle diameter of 5 µm and an ion exchange capacity of about 20 µeq/g.

The anion exchanger obtained as described above was filled in the same column as used in Example 8 and measurement was made in the same manner as in Example 8.

EXAMPLE 10

1,4-BGE was introduced to the polyvinyl alcohol-base resin prepared in Example 8 as a substrate in the same formulation as in Example 8.

100 g of the polymer having introduced therein to a glycidyl group-containing group, 10 g of pyridine, and 500 ml of water were charged in a 1 l-volume three-neck flask equipped with a nitrogen inlet tube and a stirrer and stirred at 40° C. for 1 hour to introduce tertiary heterocyclic amine to the substrate to prepare an anion exchanger. This was washed with 1N hydrochloric acid and with 1N aqueous sodium hydroxide solution by providing intervention of water washing between respective washing operations. Thereafter, the anion exchanger was immersed in a 1N aqueous sodium hydroxide solution and treated at 60° C. for 5 hours, followed by water washing and drying. The thus-obtained anion exchanger had a mean particle diameter of 5 µm and an ion exchange capacity of about 20 µeq/g.

The anion exchanger obtained as described above was filled in the same column as used in Example 8 and measurement was made in the same manner as in Example 8.

Example 11

1,4-BGE was introduced to the polyvinyl alcohol-base resin prepared in Example 8 as a substrate in the same formulation as in Example 8.

100 g of the polymer having introduced therein to a glycidyl group-containing group, 75 ml of aqueous 1% trimethylamine solution, and 500 ml of water were charged in a 1 l-volume three-neck flask equipped with a nitrogen inlet tube and a stirrer and stirred at 40° C. for 1 hour to introduce trimethylamine to the substrate to prepare an anion exchanger. This was washed with 1N hydrochloric acid and with 1N aqueous sodium hydroxide solution by providing intervention of water washing between respective washing operations. Thereafter, the anion exchanger was immersed in a 1N aqueous sodium hydroxide solution and treated at 60° C. for 5 hours, followed by water washing and drying. The thus-obtained anion exchanger had a mean particle diameter of 5 $\mu$m and an ion exchange capacity of about 20 $\mu$eq/g.

The anion exchanger obtained as described above was filled in the same column as used in Example 8 and measurement was made in the same manner as in Example 8.

EXAMPLE 12

1,4-BGE was introduced to the polyvinyl alcohol-base resin prepared in Example 8 as a substrate in the same formulation as in Example 8.

100 g of the polymer having introduced therein to a glycidyl group-containing group, 150 ml of aqueous 1% triethylamine solution, and 500 ml of water were charged in a 1 l-volume three-neck flask equipped with a nitrogen inlet tube and a stirrer and stirred at 40° C. for 1 hour to introduce triethylamine to the substrate to prepare an anion exchanger. This was washed with 1N hydrochloric acid and with 1N aqueous sodium hydroxide solution by providing intervention of water washing between respective washing operations. Thereafter, the anion exchanger was immersed in a 1N aqueous sodium hydroxide solution and treated at 60° C. for 5 hours, followed by water washing and drying. The thus-obtained anion exchanger had a mean particle diameter of 5 $\mu$m and an ion exchange capacity of about 20 $\mu$eq/g.

The anion exchanger obtained as described above was filled in the same column as used in Example 8 and measurement was made in the same manner as in Example 8.

EXAMPLE 13

As the substrate resin to which an ion exchange group was to be introduced, the styrene/divinylbenzene-base resin prepared by the following method was used. That is, a uniformly mixed solution containing 105 g of acetoxystyrene, 70 g of m-divinylbenzene, 75 g of toluene, and 3.5 g of 2,2'-azobis(isobutyronitrile) was suspended 1,250 ml of water having dissolved therein 10% polyvinyl alcohol and the mixture was homogenized. Then, the homogenate was transferred into a 2 l-volume separable flask and polymerized at 70° C. for 6 hours to obtain particulate polymer. The polymer was filtered, washed with water and with acetone, air-dried and classified by air classification to obtain particles of 3 to 6 $\mu$m in diameter.

100 g of the dry polymer obtained above was suspended 1,500 ml of water. 1,500 ml of 50% methanol solution dissolved therein 150 g of KOH was added to the suspension, and stirred at 50 degree for 6 hours to saponify. Resulting polymer was washed with water and with acetone, and dried to obtain 135 g of polymer.

Into 2 l-volume three-neck flask equipped with a nitrogen inlet tube and a stirrer, 100 g of the dry polymer obtained above, 400 g of 1,4-BGE, 300 ml of dimethyl sulfoxide, and 65 ml of water were charged. The resulting mixture was stirred at 35° C. for 16 hours under nitrogen stream to introduce a glycidyl group-containing group into the polymer substrate. After the introduction, the polymer was washed with dimethyl sulfoxide and with water and then dried by a vacuum dryer. The mass of the dried polymer was 105 g and thus, the increment from the original substrate was 5%.

Into a 1 l-volume three-neck flask equipped with a nitrogen inlet tube and a stirrer, 100 g of the polymer having introduced thereinto a glycidyl group-containing group, 8 g of 1-methylpiperidine, and 500 ml of water were charged. The resulting solution was stirred at 40° C. for 4 hour under nitrogen stream to introduce a tertiary heterocyclic amine group, thereby preparing an anion exchanger. This anion exchanger was washed in the same manner as in Example 8 to obtain an anion exchanger.

The anion exchanger was filled in the same column as used in Example 8 and measurement was performed in the same manner as in Example 8.

COMPARATIVE EXAMPLE 6

Using a commercially available column for hydroxide eluents (pellicular-type ion exchanger having introduced therein tertiary alkanolamine), measurement was performed in the same manner as in Example 8.

Evaluation:

Table 2 shows the kind of the tertiary amine introduced in Examples 8 to 13 and Comparative Example 6, the difference between retention time of fluoride ion and that of water dip, resolution between chloride ion and nitrite ion, and the retention time of phosphate ion. The difference between the retention time of fluoride ion and that of water dip was obtained by taking the top point of each peak as a retention time. The resolution between chloride ion and nitrite ion, R, was obtained according to the following equation:

$$R=2\times(t_2-t_1)/(w_1+w_2)$$

Where $t_1$ and $t_2$ represent each a retention time, and $w_1$ and $w_2$ represent each a peak width.

TABLE 2

|  | Introduced tertiary amine | Difference between fluoride ion and water dip (minute) | Resolution between chloride ion and nitrite ion (R) | Retention time of phosphate ion (minute) |
| --- | --- | --- | --- | --- |
| Example 8 | 1-Methylpiperidine | 1.00 | 5.2 | 15.6 |
| Example 9 | 1-Methylpyrrolidine | 0.95 | 5.0 | 15.2 |

TABLE 2-continued

|  | Introduced tertiary amine | Difference between fluoride ion and water dip (minute) | Resolution between chloride ion and nitrite ion (R) | Retention time of phosphate ion (minute) |
|---|---|---|---|---|
| Example 10 | Pyridine | 0.90 | 5.0 | 15.8 |
| Example 11 | Trimethylamine | 0.79 | 3.4 | 16.0 |
| Example 12 | Triethylamine | 0.68 | 3.2 | 14.1 |
| Example 13 | 1-Methylpiperidine | 0.85 | 5.5 | 19.6 |
| Comparative Example 6 | Alkanolamine | ND* | 1.8 | 34.0 |

ND*: Impossible to measure because peaks overlapped

Although the commercially available column shown in Comparative Example 6 had a retention time of phosphate ion which was extremely redundant as long as 30 minutes or more, fluoride ion overlapped water dip and the separation between chloride ion and nitrite ion was insufficient. On the contrary, in the case of the column for suppressor system ion chromatography provided with the anion exchanger prepared by introducing tertiary heterocyclic amine as described in Examples 8, 9 and 10 according to the present invention, it can be seen that even when setting the retention time of phosphate ion, which is difficult to elute, to 14 to 16 minutes, fluoride ion can be sufficiently separated from water dip and that chloride ion and nitrite ion can be sufficiently separated from each other. It can be said that this is significantly improved as compared with the column provided with the anion exchangers having introduced therein acyclic tertiary amines as described in Examples 11 and 12. Example 13 suggests that the substrate resin is not limited to polyvinyl alcohol-based resins but heterocyclic amines can be effectively introduced to other resins.

EXAMPLE 14

A uniformly mixed solution containing 100 g of vinyl acetate, 180 g of triallyl isocyanurate, 150 g of butyl acetate and 10 g of 2,2'-azobis(isobutyronitrile), and 1,400 μl of water having dissolved therein a small amount of polyvinyl alcohol and sodium phosphate were charged into a 5 l-volume three-neck flask equipped with a reflux condenser and the resulting mixed solution was stirred for 10 minutes. Subsequently, while stirring under nitrogen stream, polymerization was performed at 60° C. for 16 hours to obtain a particulate polymer. This polymer was filtrated, washed, extracted with acetone, dried, charged together with 3 l of caustic soda into a 5 l-volume three-neck flask equipped with a reflux condenser, a nitrogen inlet tube and a stirrer, and saponified while stirring at 15° C. for 20 hours under nitrogen stream. The resulting polymer was again filtered, washed and dried. In the polyvinyl alcohol copolymer obtained by the saponification, the density of hydroxyl group was 2.1 meq/g. Using this as a substrate, an anion exchanger was manufactured through the following procedure.

Into 2 l-volume three-neck flask equipped with a nitrogen inlet tube and a stirrer, 100 g of the dry polymer obtained above, 50 g of 1,4-BGE and 1,000 ml of dimethyl sulfoxide were charged. The resulting mixture was stirred at 35° C. for 16 hours under nitrogen stream to introduce a glycidyl group-containing group into the polymer substrate. After the introduction, the polymer was washed with dimethyl sulfoxide and water and then dried by a vacuum dryer. The mass of the dried polymer was 104 g and thus, the increment from the original substrate was 4%.

Into a 2 l-volume three-neck flask equipped with a nitrogen inlet tube and a stirrer, 100 g of the polymer having introduced thereinto a glycidyl group-containing group, 60 ml of a 1% aqueous triethylamine solution and 1,000 ml of water were charged. The resulting solution was stirred at 50° C. for 4 hours under nitrogen stream to introduce an amine group, thereby preparing an anion exchanger. This anion exchanger was washed with methanol, 1N hydrochloric acid and 1N caustic soda, by providing intervention of water washing between respective washing operations. Thereafter, the anion exchanger was immersed in 0.5 M sodium carbonate and treated at 60° C. for 5 hours, followed by water washing and drying. The thus-obtained anion exchanger had a particle diameter of 5 μm and an ion exchange capacity of about 50 μeq/g.

100 g of the above anion exchanger and 1,000 ml of 1 M sodium carbonate were charged in a 2 l-volume three-neck flask equipped with a stirrer and treated at 98° C. for 1, 2, 3 and 6 hours, followed by washing and drying to obtain various kinds of anion exchangers with controlled retention times, respectively.

Figure 8:
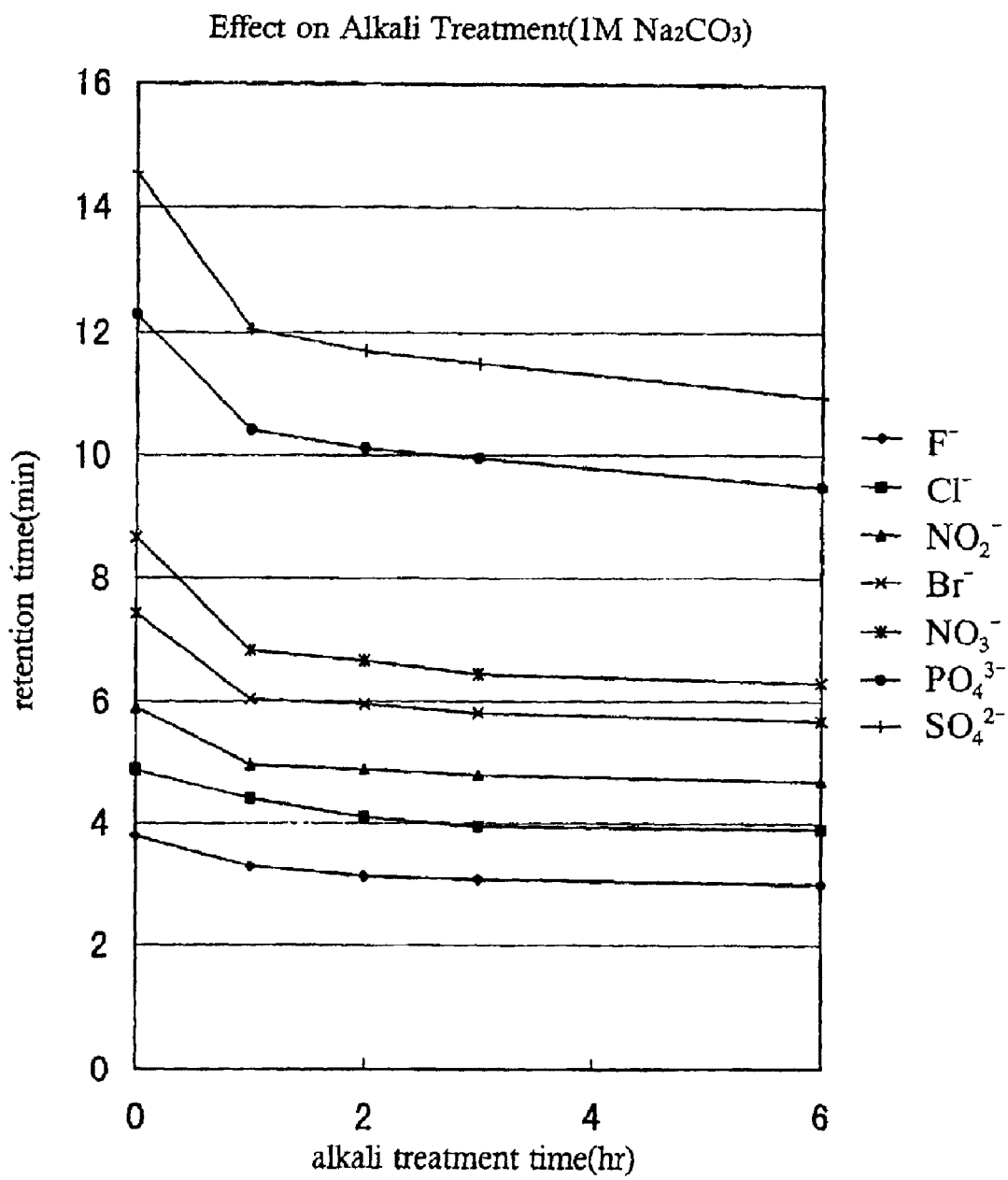
FIG. 8 is a graph illustrating the relationships between the alkali treatment time and anion retention time in Example 14 and Comparative Example 7, respectively.

The anion exchangers obtained above were each filled under pressure in a polyether ether ketone resin (PEEK)-made column having an inside diameter of 4.6 mm and a length of 150 mm to prepare anion exchange columns. Using MIC-20 (manufactured by Metrohm Ltd.) equipped with a suppressor as the ion chromatograph, a mixed aqueous solution of 1.8 mM sodium carbonate and 1.7 mM sodium hydrogencarbonate as the eluent was passed through at 1.0 ml/min and 30 μl of an aqueous solution containing 2 mg/l of $F^-$, 5 mg/l of $Cl^-$, 10 mg/l of $NO_2^-$, 10 mg/l of $Br^-$, 10 mg/l of $NO_3^-$, 10 mg/l of $PO_4^{3-}$ and 10 mg/l of $SO_4^{2-}$ was injected as a standard solution into the ion chromatograph while passing through. FIG. 8 shows changes with time in retention time of each ion by the alkali treatment.

COMPARATIVE EXAMPLE 7

Anion exchanger was produced in the same manner as in Example 14 until the quaternary ammonium group was introduced except that thereafter no alkali treatment was performed. The anion exchanger was filled in a column in the same manner as in Example 14 to fabricate a column for ion chromatography. FIG. 8 plots the retention time of each ion at time 0 hr of the alkali treatment.

EXAMPLE 15

1,4-BGE was introduced to the polyvinyl alcohol-base resin prepared in Example 14 as a substrate in the same formulation as in Example 14.

100 g of the polymer having introduced therein to a glycidyl group-containing group, 4 g of 1-methylpiperidine, and 500 ml of water were charged in all-volume three-neck flask equipped with a nitrogen inlet tube and a stirrer and stirred at 40° C. for 1 hour to introduce tertiary heterocyclic amine to the substrate to prepare an anion exchanger. This was washed with 1N hydrochloric acid and with 1N aqueous sodium hydroxide solution by providing intervention of water washing between respective washing operations. Thereafter, the anion exchanger was immersed in 1N caustic soda and treated at 98° C. for 3, 6 and 9 hours, respectively, followed by water washing and drying to obtain various anion exchangers with controlled retention times, respectively.

Figure 9:
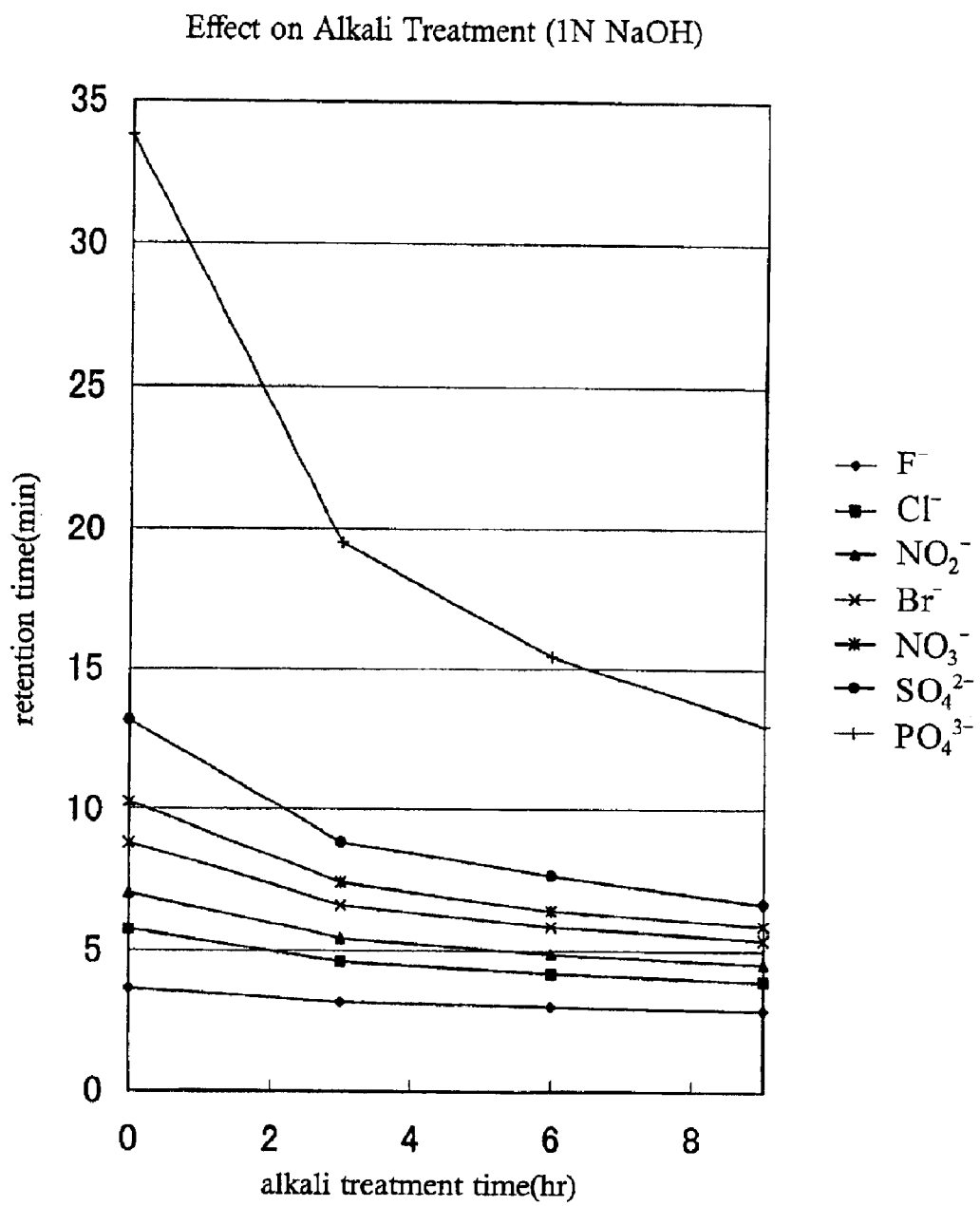
FIG. 9 is a graph illustrating the relationships between the alkali treatment time and anion retention time in Example 15 and Comparative Example 8, respectively.

The anion exchanger obtained as described above was filled in the same column as used in Example 14 and measurement was made in the same manner as in Example 14 except that 18 mM aqueous NaOH solution was used as an eluent and the column temperature was set to 35° C. FIG. 9 shows changes with time in retention time of each ion by the alkali treatment.

COMPARATIVE EXAMPLE 8

Anion exchanger was produced in the same manner as in Example 15 until the quaternary ammonium group was introduced except that thereafter no alkali treatment was performed. The anion exchanger was filled in a column in the same manner as in Example 15 to fabricate a column for ion chromatography. FIG. 9 plots the retention time of each ion at time 0 hr of the alkali treatment.

EXAMPLE 16

In a 300 ml beaker, 100 g of glycerol dimethacrylate, 50 g of n-hexyl alcohol, and 1.5 g of 2,2'-azobis (isobutyronitrile) were weighed and the mixture was subjected to an ultrasonic treatment for 2 minutes in an ultrasonic cleaner and further was mixed for 10 minutes with a stirrer. The mixture was transferred into a 1 l-volume reactor for homogenizing, and 333 ml of aqueous 2% polyvinyl alcohol (KURARAY POVAL PVA-224 manufactured by KURARAY CO., LTD.) and 2% NaCl solution were added. The mixture was stirred for 40 minutes at room temperature using a homogenizer. Then, this was transferred into a reactor equipped with a stirrer and the temperature controller was set to 63° C. (external temperature) and heated as was for 6 hours or more to obtain crosslinked gel that was insoluble in water and organic solvents. The gel was centrifuged and the precipitates were collected, washed with 500 ml of water and with 500 ml of ethanol, air-dried, and then air-classified to obtain particles of from 3 to 6 $\mu$m in particle diameter. The particles were converted into anion exchanger by the following procedures.

20 g of the above dried polymer, 40 g of 1,4-BGE, and 40 g of 1N aqueous NaOH solution were charged in a 300 ml-volume three-neck flask and stirred at 30° C. for 3 hours to introduce a glycidyl group-containing group to the polymer substrate. The polymer after the introduction was washed with 100 ml of water and with 100 ml of acetone, and dried in a vacuum drier.

10 g of the polymer having introduced therein the glycidyl group-containing group, 7.5 g of 1-methylpiperidine, 45 g of 1,4-dioxan were charged in a 300 ml-volume three-neck flask and stirred at 35° C. for 1 hour to obtain an anion exchanger having introduced therein an amino group. This was washed twice with 100 ml of acetone, once with 100 ml of water, once with 100 ml of 0.5N HCl, once with 100 ml of water, twice with 100 ml of 0.1N NaOH and three times with 100 ml of water.

10 g of the above anion exchanger and 100 ml of 0.5N-NaOH were charged in a 300 ml-volume three-neck flask equipped with a stirrer and treated at 50° C. for 2, 4 and 6.5 hours, respectively, followed by washing and drying to obtain various anion exchangers with controlled retention time.

Figure 10:
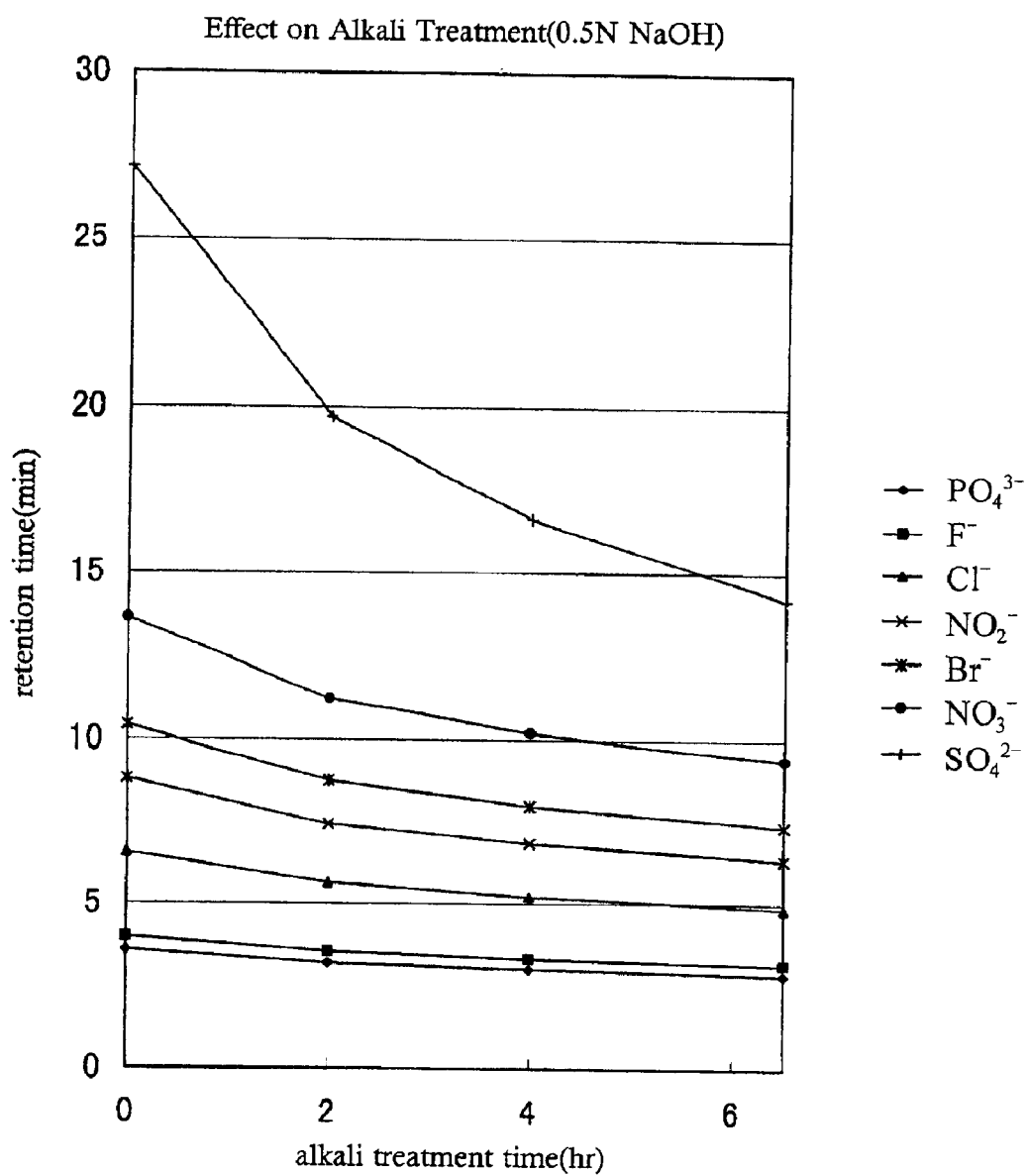
FIG. 10 is a graph illustrating the relationships between the alkali treatment time and anion retention time in Example 16 and Comparative Example 9, respectively.

The anion exchangers were each filled under pressure in a stainless column of 4.6 mm in inside diameter×100 mm in length to fabricate a column for anion analyzing liquid chromatography. This was analyzed by non-suppressor system ion chromatography by passing therethrough 8 mM p-hydroxybenzoic acid (adjusted to pH 4.1 with Bis-Tris)+2 mM phenylboric acid at 1.0 ml/min as an eluent at a column temperature of 40° C. to analyze anions. As a standard solution, 30 $\mu$l of an aqueous solution containing 2 mg/l of $F^-$, 5 mg/l of $Cl^-$, 10 mg/l of $NO_2^-$, 10 mg/l of $Br^-$, 10 mg/l of $NO_3^-$, 10 mg/l of $PO_4^{3-}$ and 10 mg/l of $SO_4^{2-}$ was injected into the ion chromatograph. FIG. 10 shows changes with time in retention time of each ion by the alkali treatment.

COMPARATIVE EXAMPLE 9

Anion exchanger was produced in the same manner as in Example 16 until the quaternary ammonium group was introduced except that thereafter no alkali treatment was performed. The anion exchanger was filled in a column in the same manner as in Example 16 to fabricate a column for ion chromatography. FIG. 10 plots the retention time of each ion at time 0 hr of the alkali treatment.

What is claimed is:

1. A porous polymer particle comprising a polymer substrate having ester bonds, wherein the polymer substrate having ester bonds is (1) a polyvinyl alcohol substrate comprising a copolymer of a carboxylic acid vinyl ester and an isocyanurate-base crosslinking monomer, a part of the ester groups being saponified into a hydroxyl group or hydroxyl groups, (2) a substrate obtained by polymerizing one or more monomers selected from the group consisting of acrylate- and methacrylate-base crosslinking monomers each having a hydroxyl group, or (3) a substrate comprising a copolymer having a hydroxyl group obtained by saponifying a part of a copolymer of an alkanoyloxystyrene and divinylbenzene, and wherein a group containing a quaternary ammonium structure is connected to the substrate through a spacer molecule having three or more atoms between the surface of the substrate and an ion exchange group.

2. A porous polymer particle comprising a polymer substrate having ester bonds, wherein the polymer substrate having ester bonds is a polyvinyl alcohol substrate comprising a copolymer of a carboxylic acid vinyl ester and an isocyanurate-base crosslinking monomer, a part of the ester groups being saponified into a hydroxyl group or hydroxyl groups, and wherein a group containing a quaternary ammonium structure is connected to the substrate through a spacer molecule.

3. A porous polymer particle comprising a polymer substrate having ester bonds, wherein the polymer substrate having an ester bond is a substrate obtained by polymerizing one or more monomers selected from the group consisting of acrylate- and methacrylate-base crosslinking monomers each having a hydroxyl group, and wherein a group containing a quaternary ammonium structure is connected to the substrate through a spacer molecule.

4. The porous polymer particle as claimed in claim 1, wherein the polymer substrate having an ester bond is a substrate comprising a copolymer having a hydroxyl group obtained by saponifying a part of a copolymer of an alkanoyloxystyrene and divinylbenzene.

5. Alkali-resistant, high-strength porous polymer particle obtained by reacting a polyvinyl alcohol-base copolymer obtained by saponifying a part of the ester bonds in the copolymer of a carboxylic acid vinyl ester and an isocyanurate-base crosslinking monomer in an alkaline solution to convert into a hydroxyl group or hydroxyl groups, with a compound having two or more glycidyl groups in the molecule to introduce a glycidyl group-containing group such that the mass after the reaction is 103 to 140 assuming that the mass of the polyvinyl alcohol-base copolymer is 100 and then reacting the product with a nitrogen-containing compound that is derived into a group having a quaternary ammonium structure.

6. A porous polymer particle comprising a porous polymer or porous polymer particle comprising a polymer substrate having an ester bond to which a group having a quaternary ammonium structure is connected through a spacer molecule having three or more atoms between the surface of the substrate and an ion exchange group, the porous polymer or porous polymer particle being treated with an alkaline solution to decompose the ester group in the substrate to generate a hydroxyl group and/or a carboxyl group on a surface of the substrate.

7. The porous polymer particle as claimed in claim 6, wherein the polymer substrate having an ester bond is (1) a polyvinyl alcohol substrate comprising a copolymer of a carboxylic acid vinyl ester and an isocyanurate-base crosslinking monomer, a part of the ester groups being saponified into a hydroxyl group or hydroxyl groups, (2) a substrate obtained by polymerizing one or more monomers selected from the group consisting of acrylate- and methacrylate-base crosslinking monomers each having a hydroxyl group, or (3) a substrate comprising a copolymer having a hydroxyl group obtained by saponifying a part of a copolymer of an alkanoyloxystyrene and divinylbenzene.

8. The porous polymer particle as claimed in claim 1, 5 or 6, wherein the group containing a quaternary ammonium structure is derived from the reaction of an epoxy group and a compound selected from a group consisting of trialkylamine, dialkylalkanolamine, N-alkyldialkanolamine, trialkanolamine, and aromatic or non-aromatic nitrogen-containing heterocyclic compounds.

9. A porous polymer particle comprising an alkali-resistant polymer substrate selected from a polyvinyl alcohol substrate comprising a copolymer of a carboxylic acid vinyl ester and an isocyanurate-base crosslinking monomer, a part of whose ester groups is saponified into a hydroxyl group or groups and a copolymer of alkanoyloxystyrene and divinylbenzene, a part of which is saponified to have a hydroxyl group or groups, wherein the substrate is connected with a group containing a quaternary ammonium structure derived from an aromatic or non-aromatic nitrogen-containing heterocyclic compound through a spacer molecule.

10. The porous polymer particle as claimed in claim 8, wherein the aromatic or non-aromatic nitrogen-containing heterocyclic compound is a compound selected from the group consisting of a pyridine compound represented by formula (1):

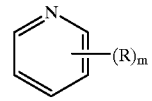

(1)

(wherein R represents an alkyl or alkoxy group having 1 to 5 carbon atoms, which is optionally substituted with a hydroxyl group or a halogen atom, and m is an integer of 0 to 5, provided that when m is 2 or more, plural R's may be the same or different), a 1-alkylpyrrolidine compound represented by formula (2):

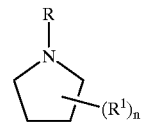

(2)

(wherein R represents an alkyl group having 1 to 5 carbon atoms, which is optionally substituted with a hydroxyl group or a halogen atom, $R^1$ represents a hydroxyl group or an alkyl group or alkoxy group having 1 to 5 carbon atoms, which is optionally substituted with a hydroxyl group, and n is an integer of 0 to 2), a 1-alkylpiperidine compound represented by formula (3):

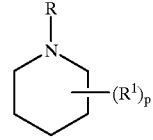

(3)

(wherein R represents an alkyl group having I to 5 carbon atoms, which is optionally substituted with a hydroxyl group or a halogen atom, $R^1$ represents a hydroxyl group or an alkyl group or alkoxy group having 1 to 5 carbon atoms, which is optionally substituted with a hydroxyl group, and p is an integer of 0 to 2), and a 1,4-dialkylpiperazine compound represented by formula (4):

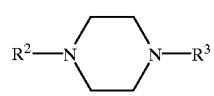

(4)

(wherein R2 and R3, which may be the same or different, independently represent a hydrogen atom, an alkyl group having 1 to 5 carbon atoms, which is optionally substituted with a hydroxyl group or a halogen atom, provided that R2 and R3 do not represent hydrogen atoms simultaneously).

11. The porous polymer particle as claimed in claim 1, 5, 6 or 9, wherein the particle has a mean particle diameter of 1 to 30 μm.

12. The porous polymer particle as claimed in claim 5, 6 or 9, wherein the particle has a mean pore diameter of 50 to 300 Å.

13. An anion exchanger comprising the porous polymer particle as claimed in any one of claims 1, 2 to 4, 6, and 7.

14. An alkali-resistant anion exchanger comprising the porous polymer particle as claimed in claim 5 or 9.

15. A method for producing an anion exchanger, comprising:
connecting a spacer molecule to a porous polymer particle comprising a polymer substrate having ester bonds,
wherein the polymer substrate having ester bonds is (1) a polyvinyl alcohol substrate comprising a copolymer of a carboxylic acid vinyl ester and an isocyanurate-base crosslinking monomer, a part of the ester groups being saponified into a hydroxyl group or hydroxyl groups, (2) a substrate obtained by polymerizing one or more monomers selected from the group consisting of acrylate- and methacrylate-base crosslinking monomers each having a hydroxyl group, or (3) a substrate comprising a copolymer having a hydroxyl group obtained by saponifying a part of a copolymer of an alkanoyloxystyrene and divinylbenzene, and
reacting the spacer molecule with a nitrogen-containing compound that is derived to a group having a quaternary ammonium structure to introduce an anion exchange group to the substrate.

16. A method for producing an anion exchanger comprising:
connecting a spacer molecule to a porous polymer particle comprising a polymer substrate having ester bonds, wherein the polymer substrate having ester bonds is a polyvinyl alcohol substrate comprising a copolymer of a carboxylic acid vinyl ester and an isocyanurate-base crosslinking monomer, a part of the ester groups being saponified into a hydroxyl group or hydroxyl groups, and
reacting the spacer molecule with a nitrogen-containing compound that is derived to a group having a quaternary ammonium structure to introduce an anion exchange group to the substrate.

17. A method for producing an anion exchanger comprising:
connecting a spacer molecule to a porous polymer particle comprising a polymer substrate having ester bonds, wherein the polymer substrate having ester bonds is a substrate obtained by polymerizing one or more monomers selected from the group consisting of acrylate- and methacrylate-base crosslinking monomers each having a hydroxyl group, and
reacting the spacer molecule with a nitrogen-containing compound that is derived to a group having a quaternary ammonium structure to introduce an anion exchange group to the substrate.

18. The method for producing an anion exchanger as claimed in claim 15, wherein the polymer substrate having ester bonds is a substrate comprising a copolymer having a hydroxyl group obtained by saponifying a part of a copolymer of an alkanoyloxystyrene and divinylbenzene.

19. A method for producing an alkali-resistant anion exchanger, comprising connecting a spacer molecule containing a glycidyl group to an alkali-resistant polymer porous particle selected from (1) a polyvinyl alcohol substrate comprising a copolymer of a carboxylic acid vinyl ester and an isocyanurate-base crosslinking monomer, a part of the ester groups being saponified into a hydroxyl group or hydroxyl groups, (2) a substrate obtained by polymerizing one or more monomers selected from the group consisting of acrylate- and methacrylate-base crosslinking monomers each having a hydroxyl group, and (3) a substrate comprising a copolymer having a hydroxyl group obtained by saponifying a part of a copolymer of an alkanoyloxystyrene and divinylbenzene through a bond that is not cleaved under an alkaline condition and reacting the glycidyl group with a nitrogen-containing compound that is derived to a group having a quaternary ammonium structure to introduce an anion exchange group into the substrate.

20. A method for producing an alkali-resistant, high-strength porous polymer particle, comprising reacting a polyvinyl alcohol-base copolymer obtained by saponifying a part of the ester bonds in the copolymer of a carboxylic acid vinyl ester and an isocyanurate-base crosslinking monomer in an alkaline solution to convert into a hydroxyl group or hydroxyl groups, with a compound having two or more glycidyl groups in the molecule to introduce a glycidyl group-containing group such that the mass after the reaction is 103 to 140 assuming that the mass of the polyvinyl alcohol-base copolymer is 100 and then reacting the product with a nitrogen-containing compound that is derived into a group having a quaternary ammonium structure.

21. A method for producing an anion exchanger, comprising connecting a tertiary amine to a polymer substrate having ester bonds through a spacer molecule to obtain an anion exchanger comprising a porous polymer (particle) and treating the porous polymer or porous polymer particle with an alkaline solution to decompose the ester groups in the substrate to generate a hydroxyl group and/or a carboxyl group on a surface of the substrate.

22. The method for producing an anion exchanger as claimed in claim 21, wherein the polymer substrate having an ester bond is (1) a polyvinyl alcohol substrate comprising a copolymer of a carboxylic acid vinyl ester and an isocyanurate-base crosslinking monomer, a part of the ester groups being saponified into a hydroxyl group or hydroxyl groups, (2) a substrate obtained by polymerizing one or more monomers selected from the group consisting of acrylate- and methacrylate-base crosslinking monomers each having a hydroxyl group, or (3) a substrate comprising a copolymer having a hydroxyl group obtained by saponifying a part of a copolymer of an alkanoyloxystyrene and divinylbenzene.

23. The method for producing an anion exchanger as claimed in claim 15, 19, or 21, wherein the group containing a quaternary ammonium structure is derived from the reaction of an epoxy group and a compound selected from a group consisting of trialkylamine, dialkylalkanolamine, N-alkyldialkanolamine, trialkanolamine, and aromatic or non-aromatic nitrogen-containing heterocyclic compounds.

24. The method for producing an alkali-resistant high-strength anion exchanger as claimed in claim 20, wherein the saponification of the polyvinyl alcohol-base polymer is carried out until from 0.5 to 5 meq/g of a hydroxyl group is generated in the polymer.

25. The method for producing an alkali-resistant high-strength anion exchanger as claimed in claim 20 or 24, comprising treating in an alkaline solution.

26. The method for producing an alkali-resistant high-strength anion exchanger as claimed in claim 25, wherein a carbonic acid salt solution is used as the alkaline solution.

27. Packing material for ion chromatography comprising the anion exchanger as claimed in claim 13.

28. A column for ion chromatography having packed therein the anion exchanger as claimed in claim 13.

29. A column for suppressor system anion chromatography having packed therein the alkali-resistant anion exchanger as claimed in claim 14.

30. A method for measuring anions, comprising using the anion exchange-packed column as claimed in claim 28.

31. A method for measuring anions by a suppressor system anion chromatography, comprising using an alkaline eluent having a pH of 9 or more and the column for anion chromatography as claimed in claim 29.

32. The method for measuring anions by a suppressor system anion chromatography as claimed in claim 31, wherein at least one selected from the group consisting of carbonate buffer, borate buffer, aqueous sodium hydroxide solution, and aqueous potassium hydroxide solution is used as the alkaline eluent having a pH of 9 or more.

33. The method for measuring anions as claimed in claim 32, wherein 20 mM or less of the aqueous sodium hydroxide solution or aqueous potassium hydroxide solution is used as the alkaline eluent under an isocratic condition.

34. The method for measuring anions by suppressor system anion chromatography as claimed in claim 31, further comprising adding an organic solvent in a ratio of 50 mass % or less to the alkaline eluent.

35. The method for measuring anions as claimed in claim 34, wherein acetone, acetonitrile or methanol is used as the organic solvent.

* * * * *